United States Patent [19]

Lurie et al.

[11] Patent Number: 5,618,665
[45] Date of Patent: *Apr. 8, 1997

[54] ENZYMATIC FLUOROMETRIC ASSAY FOR ADENYLATE CYCLASE

[75] Inventors: Keith G. Lurie, Minneapolis, Minn.; Phi Wiegn, Valhalla, N.Y.; Atsushi Sugiyama, Isawa-cho, Japan

[73] Assignee: Regents of the University of Minnesota, Minneapolis, Minn.

[*] Notice: The term of this patent shall not extend beyond the expiration date of Pat. No. 5,316,907.

[21] Appl. No.: 184,040

[22] Filed: Jan. 21, 1994

Related U.S. Application Data

[63] Continuation-in-part of Ser. No. 7,847, Jan. 22, 1993, Pat. No. 5,316,907.

[51] Int. Cl.$^6$ ........................................... C12Q 1/00
[52] U.S. Cl. .................... 435/4; 435/21; 435/963
[58] Field of Search ..................... 435/4, 19, 21, 435/25, 191, 195, 963, 968; 436/63, 172, 805, 811

[56] References Cited

U.S. PATENT DOCUMENTS

| | | | |
|---|---|---|---|
| 5,312,810 | 5/1994 | Wood et al. | 514/12 |
| 5,316,907 | 5/1994 | Lurie et al. | 435/4 |

OTHER PUBLICATIONS

Proc. Natl. Acad. Sci. USA, Vol. 78, No. 4, issued Apr., 1981. Rossomando et al., "Formycin 5'-triphosphate, a Fluorescent Analog of ATP, as a Substrate for Adenylate Cyclase", pp. 2278–2282.

Journal of Chromatography, vol. 400, issued 1987, Yoshioka et al., "Analyses of Adenosine and Adenine Nucleotides inBiological Materials by Fluorescence Reaction–High–Performance Liquid Chromatography", pp. 133–144.

Journal of Cyclic Nucleotide Research, vol. 7, No. 1, issed 1981, Wojcik et al., "A Simple Fluorometric Method of cAMP" Application to Studies of Brain Adenylate Cylcase Activity, pp. 27–35.

*Primary Examiner*—Ralph Gitomer
*Attorney, Agent, or Firm*—Schwegman, Lundberg, Woessner & Kluth, P.A.

[57] ABSTRACT

A method for measuring the amount of adenylate cyclase without the use of radioactive reagents is provided. The method comprises combining a sample of physiological material containing an amount of cAMP with (a) a mixture of enzymes effective to eliminate any other endogenous adenine nucleotides which may be present in the sample; and (b) an amount of alkaline phosphatase effective to eliminate any glucose-6-phosphate present in the sample. The cAMP present in said sample is then converted to AMP and the amount of AMP measured, which may then be correlated to the amount of cAMP and AC present in the sample.

16 Claims, 7 Drawing Sheets

ENZYMATIC FLUOROMETRIC ASSAY FOR ADENYLATE CYCLASE

Cross-Reference to Related Application

This application is a continuation-in-part of U.S. patent application Ser. No. 08/007,847, filed Jan. 22, 1993 now U.S. Pat. No. 5,316,907.

Background of the Invention

Adenylate cyclase (ATP pyrophosphate-lyase [cycling], AC, EC 4.6.1.1.), the catalytic protein that converts ATP to adenosine 3',5'-cyclic monophosphate (cAMP), plays a critical role in the signal transduction cascade of a number of fundamental hormones and neurotransmitters. For example, measurement of adenylate cyclase activity has been employed to study the altered physiology exhibited by transplanted human hearts and in congestive heart failure. See K. G. Lurie et at., *J. Thorac. Cardiovasc. Surg.*, 86, 195 (1983); M. R. Bristow et at., *New Engl. J. Med.*, 307, 205 (1982). (Chemical names of abbreviated compounds are given in the "Table of Abbreviations" hereinbelow).

However, a more clear elucidation of the biological role of adenylate cyclase in these and other conditions has been limited by the difficulty in monitoring accurately changes in the tissue levels of cAMP, the cyclic nucleotide that results from the reaction catalyzed by adenylate cyclase. The analytical difficulties arise because of the extremely low concentrations of 3',5'-cAMP in most mammalian tissues and the similarity of this cyclic nucleotide to other naturally occurring, potentially interfering, nucleotides that are present in several hundred to several hundred thousand times the concentration of 3',5'-cAMP.

Adenylate cyclase activity is conventionally assayed indirectly by measuring the synthesis of radioactively labeled cAMP from the substrate $\alpha$-$^{32}$P-labeled ATP as described by Y. Salomon et at., as disclosed in *Anal. Biochem.*, 58, 541 (1974) and *Adv. Cyclic Nucleotide Res.*, 10, 35 (1979). The methods employ sequential affinity chromatography with Dowex exchange resin and aluminum oxide columns to separate newly generated [$^{32}$P]cAMP from [$\alpha$-$^{32}$P]ATP. See also, C. L. Johnson et al., *Mol. Pharmacol.*, 16, 417 (1979). Although this method is sensitive, it relies upon costly radioactively labeled compounds.

Previously, Lowry et al. have developed a number of sensitive assays which can measure small amounts of biological compounds based on the fluorescence of reduced pyridine nucleotides. See O. H. Lowry et al., *A Flexible System of Enzymatic Analysis*, Harcourt Brace Jovanovich, N.Y. (1972); F. M. Matschinsky et al., *J. Histochem. Cytochem.*, 16, 29 (1968). These methods employ one or more of a series of enzymatic reactions which ultimately lead to the production of either β-nicotinamide-adenine dinucleotide phosphate (NADP$^+$) or β-nicotinamide-adenine dinucleotide (NAD+) or the reduced forms NADPH and NADH. The reduced purine nucleotides can be precisely measured at O.D. 340 nm in a photometer. One reaction, the measurement of AMP, depends upon the stimulatory effects of AMP on glycogen phosphorylase a, the enzyme that converts glycogen into glucose-6-phosphate in the presence of inorganic phosphate ($P_i$). See, E. Helmreich et al., *Biochemistry*, 52, 647 (1964); ibid., 51, 131 (1964); O. H. Lowry et al., *J. Biol. Chem.*, 239, 1947 (1964); M. Trus et al., *Diabetes*, 29, 1 (1980). Attempts to increase the analytical sensitivity and specificity for AMP or AC have involved the enzymic degradation of interfering nucleotides and/or their removal by chromatography (See N. D. Goldberg et al., *Anal Biochem*, 28, 523 (1969); B. McL. Breckenridge, *PNAS USA*, 52, 1580 (1964)). However, fluorometric assays have not been developed which can either directly or indirectly measure adenylate cyclase activity in physiological samples needed to accurately quantify AC or cAMP in µg samples at pmol or fmol levels.

Given the safety and environmental concerns associated with the use and disposal of radioactive materials used in the current methods to measure AC, a need exists for a highly sensitive nonradioactive assay to measure adenylate cyclase activity.

SUMMARY OF THE INVENTION

The present invention provides a highly sensitive, enzymatic fluorometric or spectrophotometric assay for adenylate cyclase (AC) activity present in a sample of physiological material, such as a tissue or fluid sample, which necessarily contains other adenine nucleotides, in addition to the cAMP produced from ATP by the AC present in the sample. The present invention can also be used to measure the activities of guanine regulatory proteins and cAMP specific phosphodiesterases.

The present assay method fast comprises the enzymatic destruction of the adenine nucleotides other than cAMP (ATP, ADP and AMP) in the sample with a mixture of apyrase, 5'-nucleotidase and adenosine deaminase and, preferably, the enzymatic conversion of any endogenous glucose-6-phosphate (G-6-P) in the sample to glucose with alkaline phosphatase (AP). Glucose-6-phosphate is produced by the reactions used to detect endogenous cAMP, and destruction of endogenous G-6-P improves the sensitivity of the assay. Optionally, the invention further comprises the use of either (a) glucose oxidase and α-amylase or (b) glycogen phosphorylase (which works in concert with the AP) for the removal of endogenous glycogen which would also be converted into glucose-6-phosphate during the reactions used to detect cAMP.

The cAMP is then converted to AMP with phosphodiesterase. The resulting AMP, in turn, can be quantified by a number of methodologies, such as those which employ it in the enzymatic conversion of an added substrate to NADPH. Thus, the present assay is based on the combination of the complete dephosphorylation of the non-cyclic nucleotides, followed by subsequent deamination, so that the dephosphorylation reactions are driven to completion, the dephosphorylation of glucose-6-phosphate, and optionally, with the enzymatic degradation of glycogen.

To quantify AMP, the AMP can be used to stimulate the activity of added glycogen phosphorylase a which converts added glycogen and inorganic phosphate into glucose-1-phosphate. The glucose-1-phosphate is ultimately enzymatically converted into 6-phosphogluconolactone, NADPH and H*. The NADPH concentration is then determined fluorometrically, i.e., in accord with the methodology of M. Trus et at., *Diabetes*, 29, 1 (1980).

Optionally, the 6-phosphogluconolactone can itself be further converted to 6-phosphogluconate by heating it in the presence of an aqueous medium, i.e., in situ and the 6-phosphogluconate can be converted to NADPH, H$^+$, $CO_2$: and ribulose-5-phosphate, in situ, in the presence of added NADP$^+$. The reactions and reagents employed in this embodiment of the present method are summarized on Table 1, below.

TABLE 1

AC Assay

1. Cleaning Reactions

A. Removal of Endogenous, Non-Cyclic Nucleotides a. ATP $\xrightarrow{\text{Apyrase}}$ AMP + 2 $P_i$ b. AMP + $H_2O$ $\xrightarrow{\text{5'-nucleotidase}}$ Adenosine + $P_i$ c. Adenosine + $H_2O$ $\xrightarrow{\text{Adenosine deaminase}}$ Inosine + $NH_4^+$ B. Removal of Endogenous Glucose-6-Phosphate and Glycogen a. Glycogen $\xrightarrow{\text{Glycogen phosphorylase}}$ Glucose-6-phosphate b. Glucose-6-phosphate $\xrightarrow{\text{Alkaline phosphatase}}$ Glucose c. D-glucose + $H_2O$ + $O_2$ $\xrightarrow{\text{Glucose Oxidase}}$ D-glucono-1,4-lactone + $H_2O_2$ 2. cAMP Reactions cAMP + $H_2O$ $\xrightarrow{\text{Phosphodiesterase}}$ AMP
(+)

a. Glycogen + $P_i$ $\xrightarrow{\text{Glycogen Phosphorylase a}}$ Glucose-1-phosphate b. Glucose-1-phosphate $\xrightarrow{\text{Phosphoglucomutase}}$ Glucose-6-phosphate c. Glucose-6-phosphate +

$NADP^+$ $\xrightarrow{\text{Glucose-6-phosphate dehydrogenase}}$

6-Phosphogluconolactone + NADPH + $H^+$

3. Optional Reactions d. 6-Phosphogluconolactone + $H_2O$ $\xrightarrow{\text{Heat}}$ 6-Phosphogluconate + $H^+$ e. 6-Phosphogluconate +

$NADP^+$ $\xrightarrow{\text{6-Phosphogluconate Dehydrogenase, Mg}^{2+}}$

Ribulose-5-P + NADPH + $H^+$ + $CO_2$

The production of ammonium ion in deamination reaction 1(c) drives the cleaning reaction sequence essentially to completion, preventing reformation of interfering phosphorylated nucleotides. These added steps provide for a significant unexpected improvement over previous fluorometric assays. Weign et al., *Anal. Biochem.*, 208, 217 (1993).

The physiological material which is assayed in accord with the present method is preferably obtained from a mammalian source, including tissue, blood cells, bone and physiological fluids such as urine, blood, CSF and the like and may be fresh or frozen. Lowry et al., *A Flexible System of Enzymatic Analysis*, Hareout Brace Jovanovich, N.Y. (1972). The method of the present invention is sensitive enough to measure cAMP in small biopsy samples weighing less than 0.1 mg and can be adapted to measure less than 1 fmol cAMP/sample. Preferably, the cAMP in the sample is provided in situ, by the conversion of endogenous and/or exogenously added ATP to cAMP by endogenous adenylate cyclase (AC).

Thus, in a preferred embodiment, the present invention comprises the steps of:

(a) combining a sample of a physiological material comprising cAMP, glucose-6-phosphate and at least one other noncyclic adenine nucleotide, i.e., selected from the group consisting of ATP, ADP, AMP and mixtures thereof; with an aqueous buffer comprising a mixture of 5'-nucleotidase, apyrase, adenosine deaminase, and alkaline phosphatase so that said noncyclic adenine nucleotide (the ATP, ADP and/or AMP) is destroyed and glucose-6-phosphate is destroyed; and optionally, combining the reaction mixture with either (1) a mixture of glucose oxidase and α-amylase or (2) glycogen phosphorylase a so that all endogenous glycogen is destroyed, while the cAMP is retained in the reaction mixture;

(b) combining the reaction mixture with phosphodiesterase, so that said cAMP is converted to AMP;

(c) contacting said AMP with glycogen phosphorylase a in the presence of glycogen and inorganic phosphate so that glucose-1-phosphate is produced in said reaction mixture;

(d) enzymatically converting the glucose-1-phosphate into 6-phosphogluconolactone, NADPH and $H^+$ in said reaction mixture; and (e) fluorometrically measuring the concentration of NADPH in said reaction mixture; and correlating said concentration of NADPH with the concentration of AC, cAMP or AMP in said sample.

The correlation of the end concentration of NADPH to the AMP concentration is simplified by our finding that the stimulation of glycogen phosphorylase a by cAMP and AMP is similar in magnitude. In situations in which the cAMP in the sample is produced from endogenous or exogenous ATP by endogenous AC, said AC activity at any time point in the conversion reaction can also be measured (e.g., in pmol/mg of tissue), for example, following stimulation of AC activity by endogenous agonists.

Preferably, following step (a), the enzymes used in the cleaning reaction are deactivated, i.e., by heating or by the addition of acid or base.

Preferably, an aqueous "cAMP mixture" of phosphodiesterase, glycogen phosphorylase a, glucose-1,6-diphosphate, inorganic phosphate, glycogen, $NADP^+$, glucose-6-phosphate dehydrogenase, phosphoglucomutase and $Mg^{2+}$ is added to the reaction mixture, following the cleaning reactions of step (a), which carry out steps (b), (c) and (d), sequentially, in situ.

Optionally, the concentration of NADPH which is generated in step (d) can be increased by sequentially converting the 6-phosphogluconolactone to 6-phosphogluconate by heating the reaction mixture of step (d), and then reacting the 6-phosphogluconate with added $NADP^+$ and 6-phosphogluconate dehydrogenase in the presence of $Mg^{2+}$ to yield ribulose-5-phosphate, NADPH, $H^+$ and $CO_2$, as shown in Table 1, hereinabove.

Alternatively, the effective concentration of NADPH which is generated in step (d) can be increased in orders of magnitude by employing it in a cycling reaction system. One such reaction system converts NADPH added to α-ketoglutarate into $NADP^+$ and glummate. The $NADP^+$ in turn converts added glucose-6-phosphate into 6-phosphogluconolactone and NADPH. As described above, the 6-phosphogluconolactone can be hydrolyzed ($H_2O$, heat) and converted to ribulose-5-P and NADPH, using 6-phosphogluconate dehydrogenase and $Mg^{2+}$. The reactions employed in this cycling system, which are described in detail in O. Lowry et al., *A Flexible System of Enzymatic Analysis*, Harcout Brace Jovanovich, N.Y. (1972), are depicted below on Table 1A.

TABLE 1A $$\alpha\text{-Ketoglutarate} + NADPH + NH_4^+ \xrightarrow{\text{Glutamate Dehydrogenase}}$$

$$\text{Glumate} + NADP^+$$

$$\text{Glucose-6-P} + NADP^+ \xrightarrow{\text{Glucose-6-P Dehydrogenase, } Mg^{2+}}$$

$$\text{6-Phosphonogluconolactone} + NADPH + H^+$$

Alternatively, as shown in Table 1B, the AMP which is produced in step (b) can be converted to ADP by combining it with ATP in the presence of myokinase. The ADP which is produced is then converted to ATP and pyruvate by combining the ADP with 2-phospho(enol)pyruvate (PEP) and pyruvate kinase (PK). The ATP is then employed in cycling reaction depicted in Table 1B.

TABLE 1B

I. ATP Reaction $$AMP + ATP \xrightarrow{\text{Myokinase}} 2\ ADP$$

$$2\ ADP + 2\ \text{Phospho (Enol) Pyruvate} \xrightarrow{\text{Pyruvate Kinase}} 2\ ATP + 2\ \text{Pyruvate}$$

II. ATP Cycling Reactions

```
Fructose                    Pyruvate
   |                           ↑
   |         ┌─── ATP ←──┐     |
   |         │           │     |
Hexokinase   │           │  Pyruvate Kinase
   |         │           │     |
   |         └──→ ADP ───┘     |
   |                           |
   ↓                    Phospho (Enol) Pyruvate
```

$$\text{Fructose-6-Phosphate} \xrightarrow{\text{Phosphoglucose isomerase}}$$

$$\text{Glucose-6-Phosphate}$$

$$\text{Glucose-6-Phosphate} + NADP^+ \xrightarrow{\text{Glucose-6-Phosphate Dehydrogenase}}$$

$$\text{6-Phosphogluconolactone} + NADPH + H^+$$

The resulting fructose-6-phosphate, produced from the excess fructose and PEP used in the cycling reaction, is converted to glucose-6-phosphate using phosphoglucose isomerase, and the glucose-6-phosphate is converted into 6-phosphogluconolactone and NADPH by exposing the G-6-P to glucose-6-phosphate dehydrogenase and $NADP^+$. The NADPH concentration can then be amplified using the cycling reaction of Table 1A.

In another alternative to the present invention, it is possible to photometrically detect the ATP signal produced as shown in Table 1B with a chemiluminescence assay that utilizes the luciferase reaction and firefly luciferin. Wulff et al., *Methods of Enzymatic Analysis*, Bergmeyer H. U., eds., VCH (1985). From this determination, it is possible to calculate the AMP concentration and thus the cAMP and adenylate cyclase concentrations. The reaction catalyzed by luciferase is depicted in Table 1C.

TABLE 1C $$ATP + D\text{-luciferin} + O_2 \xrightarrow[\text{Mg}^{2+}]{\text{luciferase}}$$

$$\text{Oxyluciferin} + PP_i + AMP + CO_2 + \text{light}^+$$

Although the rate of this reaction is very slow, the yield of the reaction (defined as the ratio of the number of emitted photons and the number of converted ATP molecules) is almost 100%. The intensity of the emitted light is directly proportional to the ATP concentration and is measured at 582 nm.

Another method to measure AMP comprises the conversion of AMP into ATP and the use of ATP to convert excess glucose into glucose-6-phosphate, which is in turn converted into 6-phosphogluconolactone and NADPH with glucose-6-phosphate dehydrogenase. See B. McL. Breckenridge, *PNAS USA*, 52, 1580 (1964). Alternatively, ATP could subsequently be amplified by converting excess added glucose and excess added $NADP^+$ to glucose-6-phosphate and NADPH as described in O. Lowry et al., *A Flexible System Enzymatic Analysis*, cited above. NADPH is then increased by orders of magnitude by the cycling system depicted in Table 1A.

The present assay method can readily be adapted to measure guanylate cyclase activity, guanosine 3', 5'-cyclic monophosphate (cGMP) and guanosine 3',5'-monophosphate (GMP). As shown in Table 1D, below, a cleaning mixture of apyrase, 5'-nucleotidase, nucleoside phosphorylase and guanase is used. In addition, alkaline phosphatase may be used to dephosphorylate compounds such as glucose-6-phosphate and noncyclic nucleotides which may increase the blank values during the measurement of cGMP. In the cleaning reactions, tissue GTP is converted to GMP plus $2P_i$, GMP plus water is converted into guanosine and $P_i$, guanosine plus $P_i$ is converted into guanine and ribose-1-phosphate and guanine plus water is converted into xanthine and ammonia. As in the cleaning reaction depicted in Table 1, the formation of ammonium (or $NH4^+$) in the final cleaning reaction drives the series of linked reactions essentially to completion, and ensures removal of the interfering nucleotides. Preferably, the enzymes used in the cleaning reactions are deactivated, e.g., by heating, prior to the phosphodiesterase step (2).

TABLE 1D cGMP Reactions

1. Cleaning Reactions $$GTP \xrightarrow{\text{Apyrase}} GMP + P$$

$$GMP + H_2O \xrightarrow{\text{5' Nucleotidase}} \text{Guanosine} + P_i$$

TABLE 1D-continued cGMP Reactions

Guanosine + Pi $\xrightarrow{\text{Nucleoside Phosphorylase}}$ Guanine + Ribose-1-P 2) Phosphodiesterase Step:

cGMP $\xrightarrow{\text{Phosphodiesterase}}$ GMP

GMP + ATP $\xrightarrow{\text{Guanine Monophosphate Kinase}}$ GDP + ADP

3) Cycling Reactions:

```
Phospho (Enol) Pyruvate           Succinate + CoA
         |                               ↑
         |          ⟶ GDP ⟵              |
  Pyruvate                         Succinic
  Kinase                           Thiokinase
         |          ⟶ GTP ⟶              |
         |                               |
         ↓                        Succinate − CoA + P_i
      Pyruvate
```

4) Indicator Reaction:

Pyruvate + NADH + H⁺ $\xrightarrow{\text{Lactate Dehydrogenase}}$ Lactate + NAD⁺

The cGMP present in the (tissue) sample is then converted to GMP with phosphodiesterase. The GMP is combined with ATP in the presence of guanine monophosphate kinase to yield guanosine 5'-diphosphate (GDP) and ADP. The GDP is employed in a cycling reaction (3) in the presence of excess PEP, succinate-CoA and inorganic phosphate ($P_i$) to yield an amount of pyruvate. This pyruvate is quantitated indirectly by adding known amounts of NADH which, in the presence of acid is converted to lactate and NAD⁺. Thus, the fluorescence of the indicator samples is decreased in direct proportion to the amount of pyruvate generated in the sample to be assayed for cGMP, GMP or guanylate cyclase. An alternative way to measure GMP is to measure the loss of ATP in reaction step 2 (guanine monophosphate kinase—Table 1D). ATP can be measured by several different techniques, some of which are described in Tables 1B and 1C.

In addition to improving assay sensitivity, measurement of adenylate cyclase activity or guanylate cyclase activity with the present enzymatic assays is significantly less costly, less time consuming, safer for the operator, and better for the environment. Thus, they offer a significant methodological advance for the measurement of adenylate cyclase or guanylate cyclase activity.

Finally, the present assay can readily be adapted to determine the amount of endogenous or exogenous phosphodiesterase in sample, such as a physiological sample. In accord with this embodiment of the invention, a single, preselected amount of cAMP is added to a sample containing an unknown concentration of phosphodiesterase. Specific inhibitors of specific phosphodiesterases can be added as needed. A standard curve is generated by adding a single, preselected excess amount of cAMP to different preselected, known amounts of phosphodiesterase. After a finite amount of reaction time (5–60 minutes) in which some but not all of the added cAMP is transformed to AMP by the phosphodiesterase, the reaction is stopped. A cAMP standard curve can by run concurrently to verify that all reactions are working adequately. A cleaning reaction is initiated to degrade all old and newly generated non-cyclic adenine nucleotides, as described above. The remaining cAMP will be inversely proportional to the native plus added phosphodiesterase. The cAMP is then measured in the usual manner, i.e., converted to AMP and assayed. See Example 11.

The present invention also provides as an article of manufacture, a kit comprising packaging material, such as a box, containing in association, separately packaged, preselected amounts of (a) apyrase, 5'-nucleotidase, adenosine deaminase and AP, optionally in association with glucose oxidase and alpha amylase or glycogen phosphorylase or (b) apyrase, 5'-nucleotidase, nucleoside phosphorylase, guanase and AP, optionally in association with glucose oxidase and alpha-amylase or glycogen phosphorylase; and wherein said kit includes instruction means which indicate that (1) said separately packaged amounts of the enzymes listed in part (a) can be used to remove the non-cyclic phosphorylated nucleotides, glucose-6-P and, optionally, glycogen as shown in Table 1(1) above, from cAMP, in assay for cAMP, AC activity, AMP or mixtures thereof, in accord with the present invention; or (2) said separately packaged enzymes listed in part (b) can be used to remove the noncyclic phosphorylated nucleotides, and glucose-6-phosphate as shown in Table 1D(1) from cGMP, in the assay for cGMP, guanylate cyclase activity, cGMP specific phosphodiesterase or GMP in accord with the present invention.

Suitable instruction means include printed labels, printed package inserts, tags, cassette tapes and the like. Suitable packaging material for the enzymes includes bottles, vials and the like. Optionally, the enzymes may be pre-mixed with an acceptable liquid vehicle, such as physiological buffer.

The methods of the present invention can also be readily adapted for use in automated analytical equipment for use in either biochemical or clinical applications either with or without utilization of the amplification steps described herein.

DETAILED DESCRIPTION OF THE INVENTION

Figure 1:
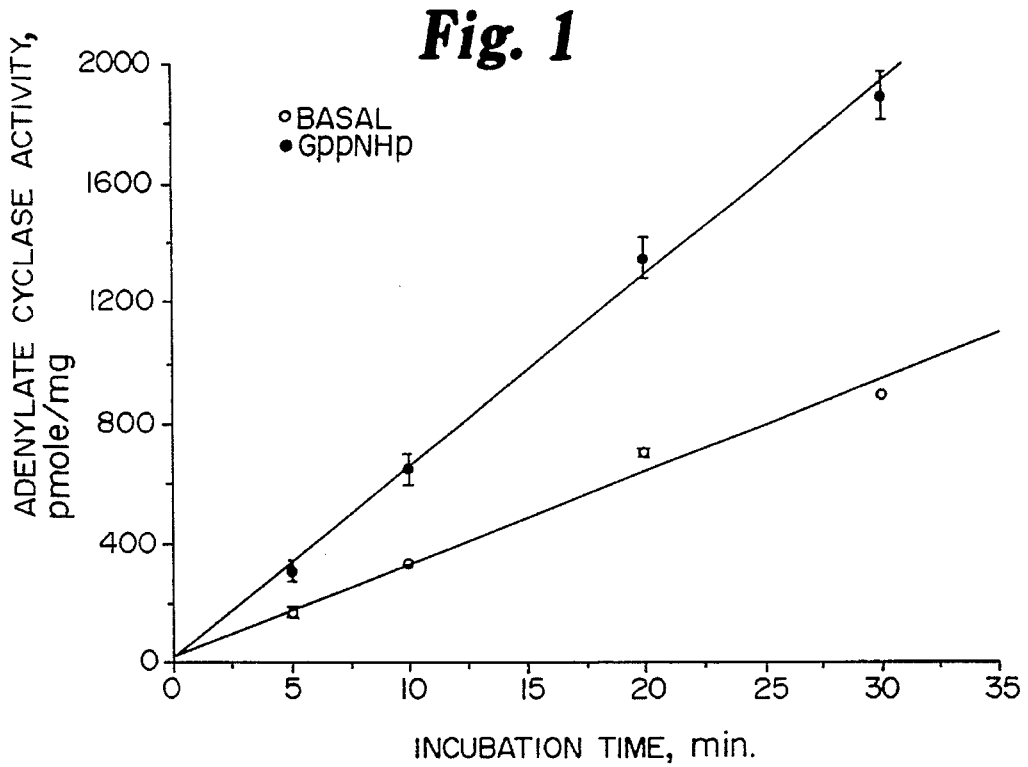
FIG. 1 is a graphical depiction of the time course of basal (o) and GppNHp (●)-stimulated tissue AC activity as measured by a prior art assay.

The present invention provides a novel, non-radioactive enzymatic fluorometric assay for adenylate cyclase activity and cAMP, as well as cAMP specific phosphodiesterase activity and the biological activity of the G regulatory proteins. The method of the present invention offers several advantages over currently available methods. Unlike the assays previously disclosed by Y. Salomon et al., in *Anal. Biochem.*, 58, 541 (1974) and *Adv. Cyclic Nucleotide Res*, 10, 35 (1979), the present assay does not utilize any radioactive material. In addition, this assay is more sensitive and simpler to perform than the previous assays.

Lowry and others have previously developed and employed a highly sensitive method to measure AMP, as disclosed by, for example, K. Lurie et al., *Ann, J. Physiol*, 253, H662–H670 (1987). AMP-stimulated phosphorylase a activity is dependent upon temperature and the concentrations of glycogen, inorganic phosphate, and glycogen phosphorylase a. See E. Heimrich et al., *Biochemistry*, 52, 131 (1964) and M. Trus et al., *Diabetes*, 29, 1 (1980). One embodiment of the present fluorometric measurement of cAMP is based on the principle that AMP, generated from the cleavage of the 3',5'-phosphodiester linkage of cAMP, will stimulate glycogen phosphorylase a activity. There was, in fact, essentially no difference between glycogen phosphorylase a activation when its stimulation with AMP was compared to its stimulation with cAMP in the presence of phosphodiesterase.

The basic cleaning step in the present fluorometric cAMP assay removes all endogenous ATP, ADP, and AMP which would otherwise substantially increase the blank. Additionally, cleaning steps can be performed which remove all endogenous glucose-6-phosphate and glycogen. These cleaning steps are important for optimal assay sensitivity. As demonstrated in the working examples, the sensitivity of this assay can also be increased by reducing the reaction volumes. It can also be increased further by varying the concentrations of glycogen and inorganic phosphate in the reaction mix, as taught by Meinrich et al. and E. Helmrich et al., *Biochemistry*, 52, 647 (1964). With the present level of sensitivity, measurement of agonist-stimulated adenylate cyclase activity is possible in mammalian tissue biopsy samples comprising as little as 10.0 μg of membrane protein. Unlike the radioactive methods, where sensitivity is limited by the specific activity of [alpha-$^{32}$P]cAMP and the volume size for chromatographic separation, there are no significant barriers to further increasing the sensitivity of the present fluorometric method. For example, cAMP has been measured with fluorometric enzyme-linked reactions which are sensitive over a broad concentration range of cAMP (1 fmol–1 mmol).

Where stimulated adenylate cyclase activity was measured in the same preparation from rabbit heart with both the modified Salomon radioactivity method and the present flourometric method without AP, the results were similar (Examples 1–2). Results with the radioactive assay are comparable to results K. Lurie et al. have previously reported using rabbit heart preparations (*J. Thorac. Cardiovasc. Surg.*, 86, 195 (1983)). Although the absolute specific activities are different when the results from the radioactive assay and the fluorometric assay utilizing glycogen phosphorylase a are compared, the fold stimulation of AC as determined using either method is similar. The differences in specific activities are most likely due to minor variations in the adenylate cyclase reaction mixes. Specifically, unlabelled cAMP is used in the radioactive assay to prevent [$^{32}$P]cAMP degradation by endogenous phosphodiesterases, whereas theophylline is used in the fluorometric assay to inhibit endogenous phosphodiesterase degradation of newly synthesized cAMP. Moreover, measurement of adenylate cyclase using the ATP:ADP cycling reaction as shown in Table 1B, revealed that the absolute specific activities were the same for both the radioactive and fluorometric assays.

Measurement of cAMP in a wide variety of mammalian and non-mammalian tissue and fluids provides a useful way to assess cell viability, endocrine-hormonal axis function, adenylate cyclase activity and phosphodiesterase activity. In addition, measurement of cAMP can be used to evaluate the activity of a number of signal transduction proteins, including, but not limited to, the family of G proteins (guanine-nucleotide binding protein) which play a major role in signal transduction, ribosomal protein synthesis, translocation of nascent proteins and other important cellular functions. Bourne et al., *Nature*, 348, 125 (1990). Furthermore, measurement of cAMP may be used in evaluating other endogenous and exogenous compounds (for example, nitrous oxide) which may alter the level of cyclic nucleotides in a particular cell, tissue, organ or body fluid.

Many hormones use cAMP as a second messenger including, but not limited to: epinephrine, norepinephrine, adrenocorticotropin (ACTH), vasopressin, glucagon, thyroxine, and thyroid-stimulating and melanocyte-stimulating hormones. These are some of the principle regulatory hormones/proteins in the living organism. The activity of all of these hormones and regulators can be measured in tissues, serum, body fluids, and in all cell cultures (cells and medium) using the described method for cAMP. Measurement of these hormones is performed in a wide variety of disease states where hormonal imbalance may lead to specific pathology.

Once a hormone or regulatory protein interacts with a specific receptor, the second messenger, in this case, cAMP, is produced through a cascade of biochemical events. The production of cAMP can also be specifically inhibited in some cases by hormones which use a decrease in cAMP as part of the specific hormonal signal-transduction pathway. The result of this regulatory protein or hormone and receptor interaction can be, but is not limited to, (1) an alteration in cell permeability secondary, for example, to changes in ion channels, (2) an alteration in the rate of enzyme catalyzed reactions sensitive to the concentration of cAMP, and (3) an alteration in the rate of protein synthesis including the synthesis and degradation of other enzymes. Measurement of cAMP can be used to directly and indirectly measure these consequences after a hormone or regulatory protein interacts with a receptor.

Specifically, cAMP can be measured in urine or blood for use as a marker for drug levels, like aminophylline or theophylline which stimulate the adrenergic nervous system by preventing the breakdown of endogenous cAMP. Measurement of cAMP in cell cultures can be used to assess specific hormones, regulatory proteins, and drugs in which cAMP represents a vital link in the signal transduction process. cAMP can also be used to assess cell viability and stability by studying cells in the absence or presence of a specific hormone or regulatory protein. For example, measurement of cAMP in liver cells (hepatocytes) by glucagon, can be used to assess hepatocyte viability. This may be useful, for example, in organ and/or cell transplantation, for example heart, liver, lung, kidney, pancreas, skin and brain cell transplantation. Measurement of the responsiveness of cells from biopsy samples after activation by a wide variety of hormones, regulatory proteins and drugs which either increase or decrease cellular cAMP levels, can be used as a way to specifically assess cell function. A specific clinical example is the use of cAMP measurement in cardiac biopsies to assess the responsiveness of the myocardium. Cardiomyopathic heart cells do not respond with the same rise in cAMP content after β-adrenergic stimulation as normal heart cells. The diagnosis of the severity of the heart disease and the efficacy of some drugs, such as β-adrenergic blockers and angiotensin converting enzyme inhibitors, can be made comparing the responsiveness of biopsy samples from normal hearts to cardiomyopathic hearts. In addition, release of cAMP either intracellularly or into the arterial or venous circulation can be used as an indicator of the response of an organ and/or tissue to a variety of different physiologic and nonphysiologic stresses such as ischemia, hypoxia, or drug or hormonal stimulation. Tissue or body fluid levels of cAMP can be measured in nearly every mammalian cell or body fluid, including blood cells and platelets, with this approach. In some tissues, cAMP levels can be measured in response to specific stimulators as an index on oncogenicity and/or invasiveness, in the case of samples of potentially tumorous cells. In other cases, measurement of cAMP can be used to determine the effectiveness of specific therapies which may alter cAMP synthesis or degradation.

The invention will be further described by reference to the following detailed examples wherein the enzymes, substrates and cofactors used were obtained from Boehringer Mannheim Co., except for apyrase and 5'-nucleotidase which were obtained from Sigma Co., St. Louis, Mo. The [alpha-$^{32}$P] ATP, $^3$H-cAMP, and Aquasol scintillation cocktail were purchased from New England Nuclear. Neutral Chromatographic Alumina WN-3 was obtained from Bio-Rad.

Ventricular membrane preparations were prepared from five male New Zealand white rabbits (weight 2.4 kg; W.O.R.K., Philomith, Oreg.) sacrificed by cervical concussion and immediate incision of the heart as previously described. Briefly, hearts were placed in ice-cold SET buffer (0.25M sucrose, 0.1 mM EDTA, 5.0 mM Tris HCl, pH 7.4). Portions (1–2 g) from the ventricular apex were minced and then homogenized in ice-cold SET buffer (1/10, w/v). The homogenate was filtered through a Nitex filter (three layers) (Tetko, Los Angeles, Calif.) and then centrifuged for 20 min. at 1000×g. The pellet was resuspended and centrifuged three more times. The final pellet was resuspended in SET buffer (1.5 mg protein/ml) and stored at −70° C. until enzyme activity was measured.

EXAMPLE 1

Radioactive Adenylate Cyclase Assay.

A volume of 1.0 μl of either $H_2O$, NaF, guanylyl-5'-imidodiphosphate (GppNHp), isoproterenol, or isoproterenol+GppNHp were added to each of five reaction tubes and maintained at 0° C. Next, 25 μl of reaction mixture A (Tris Acetate 100 mM, pH 7.4; KCl 20 mM; $MgCl_2$ 10.0 mM; phosphoenolpyruvate 20 mM; ATP 2.0 mM; GTP 0.02 mM; dithiothreitol 2.0 mM; bovine serum albumin 0.04%; cAMP 0.66 mM; pyruvate kinase 1.0 mg/ml and alpha $^{32}$P-ATP, 3000 Ci/mmole) were added to each reaction tube. Finally 25 μl of membrane suspension (40 to 45 protein) were added to each tube and the reaction was initiated by placing the tubes in a water bath at 37° C. After 30 minutes, the reaction was terminated by the addition of 300 μl of a stopping solution which contained 0.34 HCl and $^3$H-cAMP, 10,000–20,000 cpm.

Figure 2:
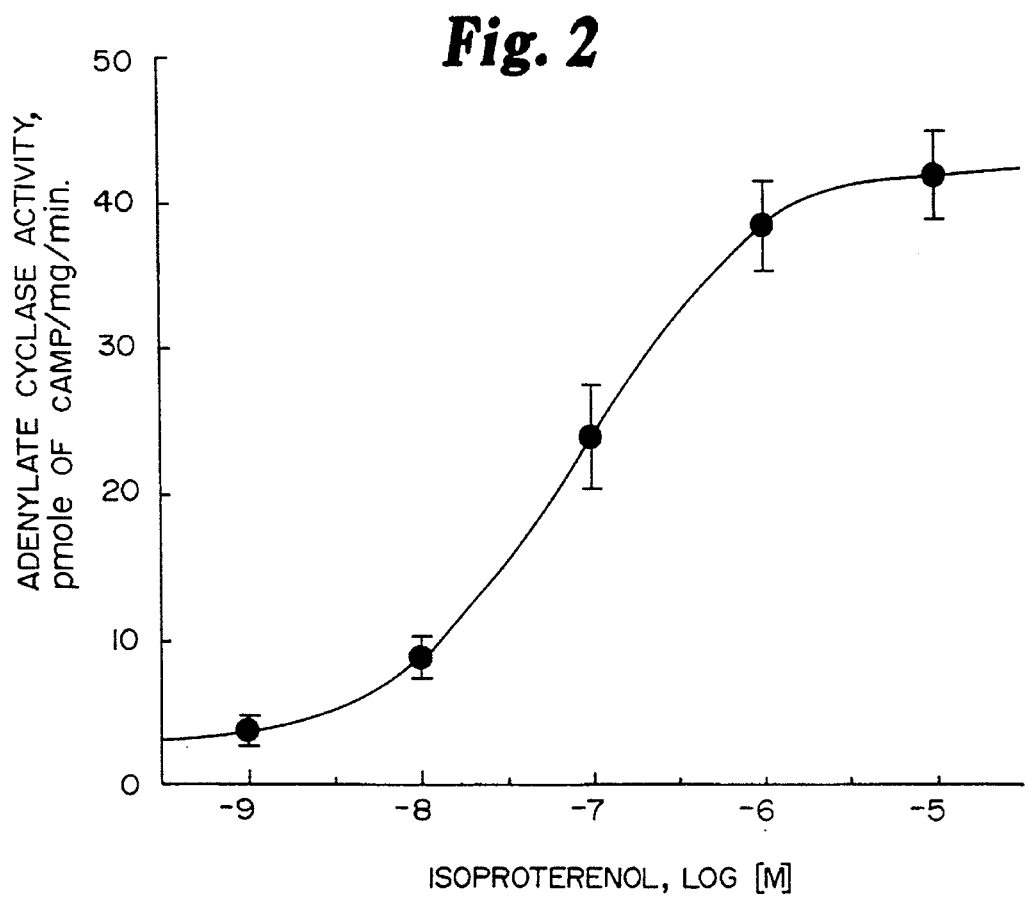
FIG. 2 is a graphical depiction of the level of tissue AC activity following stimulation of tissue AC activity by isoprotereriol, as measured by a prior art assay.

To generate the graph depicted in FIG. 2, 250 μl portions of reaction mixture A and membrane were used and 50 μl samples were removed from the 37° C. bath every 10 minutes, and stopped with 300 μl stopping solution. The assay tubes were heated at 95° C. for 5 minutes. $^{32}$P-cAMP was isolated using Dowex-alumina chromatography. Recovery, as assessed by $^3$H-cAMP, was 80–95%. All assays were conducted in triplicate. The time course of adenylate cyclase activity (n=5 different rabbit ventricular membrane preparations) is depicted in FIG. 1. Basal AC and agonist stimulated (0.1 mM GppNHp, 0.1 mM) AC are compared. Measurements of isoproterenol-stimulated AC activity (in the presence of GppNHp, a GTP analog) are shown in FIG. 2. The activity shown is (isoproterenol+GppNHp-stimulated AC activity) minus (GppNHp-stimulated activity).

EXAMPLE 2

Fluorometric Adenylate Cyclase Assay

Part A

The first part of the non-radioactive fluorescent technique for measuring adenylate cyclase activity is similar to the method described above except that theophylline, rather than unlabeled cAMP, was used to inhibit phosphodiesterase activity. A volume of 1.0 μl of either $H_2O$, NaF, guanylyl -5'-imidodiphosphate (GppNHp), isoproterenol, or isoproterenol+GppNHp was added to each of five reaction tubes and maintained at 0° C. Next, 25 μl of reaction mixture B (tris Acetate 100 mM, pH 7.4; KCl 20 mM; MgCl2 10.0 mM; phosphoenolpyruvate 20 mM; ATP 2.0 mM; GTP 0.02 mM; dithiothreitol 2.0 mM; bovine serum albumin 0.04%; theophylline 0.2 mM; pyruvate kinase 1.0 mg/ml) were added to each reaction tube. Finally, 25 μl of membrane suspension (40 to 45 μg protein) were added to each tube and the reaction was initiated by placing the tubes in a water bath at 37° C. After 30 minutes at 37° C., the reaction was stopped by the addition of 50 μl of 50 mM NaOH. The reaction mixture was heated for 5 minutes at 95° C. For cAMP standards, a known amount of cAMP was added to either 25 μl of boiled membrane preparation or 25 μl H$_2$O and then this mixture was added to 25 μl of reaction mixture B. After 30 minutes, the reaction was stopped by the addition of 50 μl of 50 mM NaOH, and the reaction mixture was heated for 5 minutes at 95° C.

Part B

Newly synthesized cAMP was measured as follows:

1. A volume of 20–40 μl of reaction product from Part A was added to 100 μl of cleaning reaction mix (Tris-HCl 50 mM, pH 8.0; MgCl$_2$ 5 mM; CaCl$_2$, 2 mM; 5'-nucleotidase 0.025 units/ml; apyrase 0.02 units/ml; adenosine deaminase 0.1 mg/ml). After 30 minutes at 37° C., the reaction was terminated by heating it at 95° C. for 5 minutes.

2. A volume of 300 μl of cAMP mix (Imidazole HCl 50 mM, pH 6.9; MgCl$_2$ 0.5 mM; EGTA 1.0 mM; BSA 0.004%; inorganic phosphate 1.5 mM; glycogen (0.1 mM of glucose reduction units), glucose-1,6-diphosphate 2 μM; NADP$^+$ 0.15 mM; dithiothreitol (DTT) 0.5 mM; phosphodiesterase (beef heart) 0.1 mg/cc; glucose-6-phosphate dehydrogenase 15 μg/ml; phosphoglucomutase 30 μg/ml; glycogen-6-phosphorylase a 6.7 μg/ml) was added to each reaction tube from Step 1. After 60 minutes at 37° C., 600 μl of 2-amino-2-methyl-1-propanol (AMP$_2$) 50 mM, pH 9.9 was added to the reaction mix and the final concentration of NADPH was measured fluorometrically.

Protein analysis was performed by the methods of Bradford et al., using bovine serum albumin as standard (M. M. Bradford et al., *Anal. Biochem.*, 72, 248 (1976)). All data was expressed as mean ±S.E.M.

Figure 3:
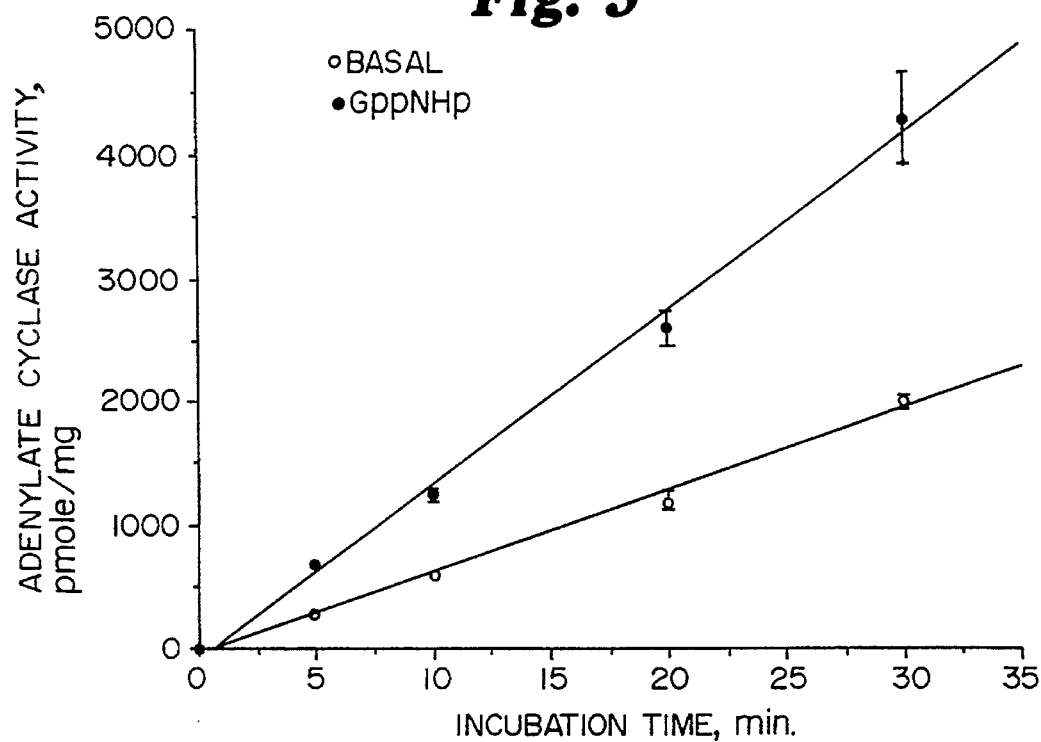
FIG. 3 is a graphical depiction of the time course of basal (o) and GppNHp (●)-stimulated tissue AC activity as measured by an embodiment of the assay of the invention.

FIG. 3 depicts the time course of AC activity (n=5 different rabbit ventricular membrane preparations) obtained using this method. To generate these data, 250 μl of reaction mixture B was added to 250 μl of plasma membrane. The reaction proceeded at 37° C. and samples (25 μl) were removed every 10 minutes. A volume of 25 μl of 0.05N NaOH was added and heated at 90° C. for 5 minutes and cAMP was measured. Basal adenylate cyclase and agonist-stimulated activity (GppNHp, 0.1 mM) are compared.

Figure 4:
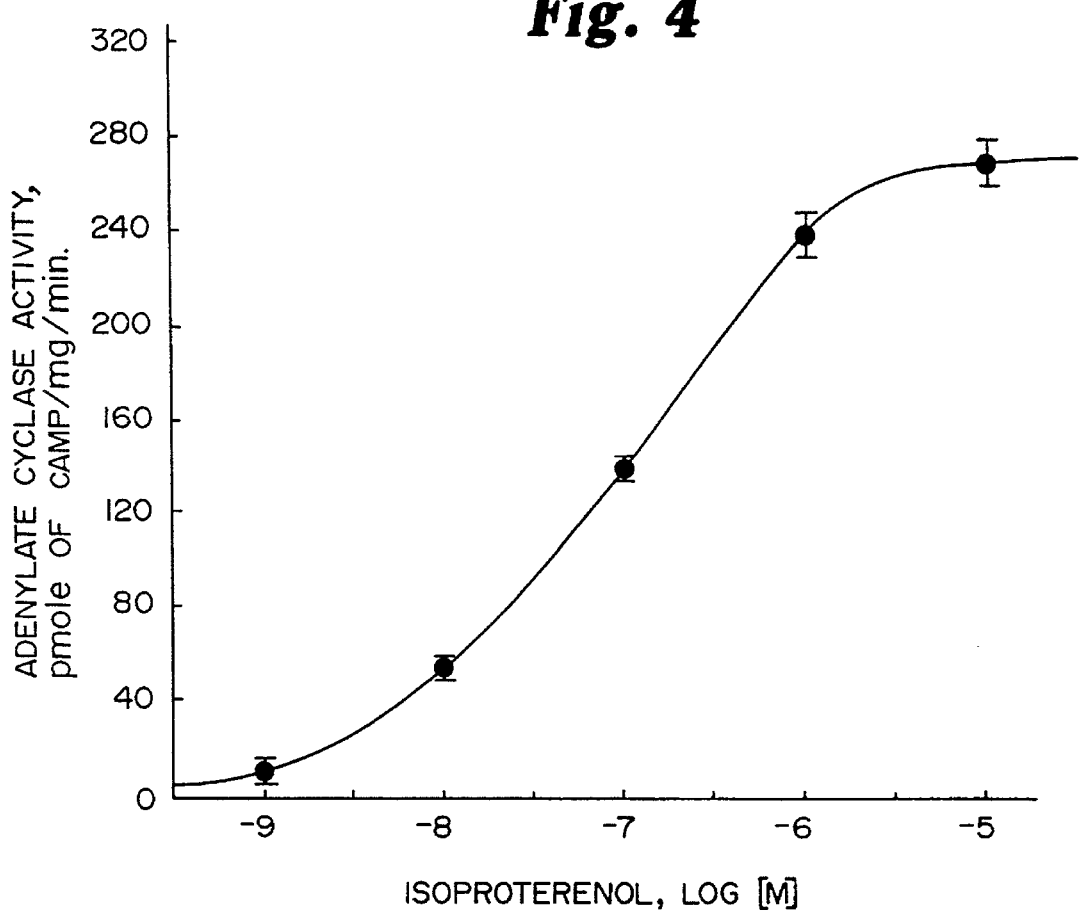
FIG. 4 is a graphical depiction of the level of tissue AC activity following stimulation of tissue AC activity by isoproterenol, as measure by an embodiment of the assay of the invention.

FIG. 4 depicts the adenylate cyclase activities in response to different doses of isoproterenol in the presence of 0.1 mM of GppNHp (n=5 different rabbit heart preparations). The activity shown here is (isoproterenol+GppNHp–stimulated adenylate cyclase activity) minus (GppNHp–stimulated activity).

The time course for adenylate cyclase activity using both radioactive and fluorometric methods yielded similar results (FIGS. 1 and 3). The absolute amount of cAMP generated/mg/minute is different with these reactions. However, when activation by GppNHp (10$^{-4}$M) is expressed as a percent of basal activity, the time courses of basal- and agonist-stimulated cAMP production are nearly identical.

Measurements of isoproterenol-stimulated adenylate cyclase activity (in the presence of GppNHp, a GTP analog) using the radioactive and fluorometric methods are shown in FIGS. 2 and 4. Although the absolute values for adenylate cyclase activity, when these results are expresses as a percent increase over basal activity ("fold stimulation"), the curves are nearly identical.

EXAMPLE 3

Effect of Theophylline on Basal Adenylate Cyclase Activity.

To investigate the effects of theophylline on basal adenylate cyclase activity, increasing concentrations of theophylline were studied (Table 2).

TABLE 2

| [Theophylline] | Basal (no isoproterenol) (pmole/mg/min.) | Fold Increase[a] | Isoproterenol Stimulated[b] (pmole/mg/min.) | Fold Increase |
|---|---|---|---|---|
| Control | 30.67 ± 8.30 | — | 51.73 ± 10.47 | — |
| 10 μM | 44.72 ± 4.61 | 1.46 | 85.58 ± 5.56 | 1.65 |
| 50 μM | 44.63 ± 5.93 | 1.46 | 93.02 ± 3.55 | 1.80 |
| 100 μM | 59.94 ± 3.63 | 1.91 | 104.21 ± 3.50 | 2.01 |
| 500 μM | 53.82 ± 4.37 | 1.75 | 102.67 ± 2.86 | 1.98 |

[a]Fold Increase = Basal activity/activity in the presence of Theophylline
[b]Isoproterenol-stimulated = Isoproterenol at 10$^{-6}$M
n = 5

With theophylline at 100–500 μM, basal activity is increased approximately 100%. However, the "fold" stimulation (agonist-stimulated activity/basal activity) of adenylate cyclase activity was constant at a given concentration of agonist (isoproterenol) in the presence of theophylline. When theophylline was added at concentrations greater than 100 μM, no significant increase in basal activity was observed.

EXAMPLE 4

Comparison of AC Assay

Table 3 demonstrates the similarities in measurement of adenylate cyclase activity after agonist stimulation when the radioactive and fluorometric assays described in Examples 1–2 were used in 5 preparations of rabbit ventricle. Although the basal activity is nearly 3 times higher in the nonradioactive method, the "fold" stimulation is similar for both receptor-mediated agonists (isoproterenol±GppNHp) as well by NaF, which directly stimulates adenylate cyclase.

TABLE 3

| Agonist | Radioactive Adenylate Cyclase Assays (n = 5) (pmoles of cAMP/mg/min) | Fold Increase[a] | Fluorescent Adenylate Cyclase Assays (n = 5) (pmoles of cAMP/mg/min) | Fold Increase |
|---|---|---|---|---|
| Basal | 20.7 ± 1.4 | — | 65.4 ± 6.8 | — |
| Iso[b] | 38.3 ± 2.3 | 1.85 | 110.0 ± 3.3 | 1.68 |
| GppNHp[c] | 64.9 ± 3.3 | 3.13 | 185.3 ± 13.7 | 2.83 |

TABLE 3-continued

| Agonist | Radioactive Adenylate Cyclase Assays (n = 5) (pmoles of cAMP/mg/min) | Fold Increase[a] | Fluorescent Adenylate Cyclase Assays (n = 5) (pmoles of cAMP/mg/min) | Fold Increase |
|---|---|---|---|---|
| Iso + GppNHp[d] | 96.9 ± 5.3 | 4.68 | 263.7 ± 9.3 | 4.03 |
| NaF[e] | 106.2 ± 3.5 | 5.13 | 346.7 ± 15.9 | 5.30 |

[a]Fold Increase = Agonist stimulated activity/Basal activity
[b]Iso = Isoproterenol at $10^{-6}$M
[c]GppNHp = 5'-Guanylyl-imidodiphosphate at $10^{-4}$M
[d]Iso + GppNHp = Isoproterenol at $10^{-6}$M plus 5'-Guanylyl-imidodiphosphate at $10^{-4}$M
[e]NaF = Sodium Fluoride at $10^{-2}$M The non-radioactive assay of Example 2 is at least 5 times more sensitive than the modified Salomon radioactive assay of Example 1. In Table 3, 5 μl of membrane preparation were used to measure adenylate cyclase activity in the non-radioactivity assay compared to 25 μl with the radioactive preparations. In a separate experiment, the volume of membrane suspension was reduced from 25 μl to 5 μl. By proportionally reducing the assay volume size, no difference in basal (58.4±3.9), isoproterenol ($10^{-6}$M) (128±7.6) or NaF ($10^{-2}$M) (331.9±42.8) stimulated activity was observed when results were compared to larger assay volumes present. EXAMPLE 5.

Stimulation of Glycogen Phosphorylase by cAMP and AMP.

A glycogen→NADPH model reaction system was prepared by combining 100 mM imadazole HCl, pH 6.9; 0.5 mM $MgCl_2$, 1.0 mM EGTA; 0.5 mM DTT; 2 μM glucose-1,6-diphosphate, 0.02% BSA, 1 mM $P_i$, 0.3 mM glycogen, 0.3 mM NADP, 0.5 μ/ml phosphodiesterase [beef heart], 10 μg/ml glucose-6-phosphate dehydrogenase, 20 μg/ml phosphoglucomutase and 1 μg/ml glycogen phosphorylase a. Ten minutes after initiation of the glycogen-phosphorylase a reaction at 25° C., either cAMP (5 μM) or AMP (5 μM) was added to 1.0 ml of the reaction mixture. Fluorometric readings were taken every 5.0 min. as described in Part B of Example 2, hereinabove.

Figure 5:
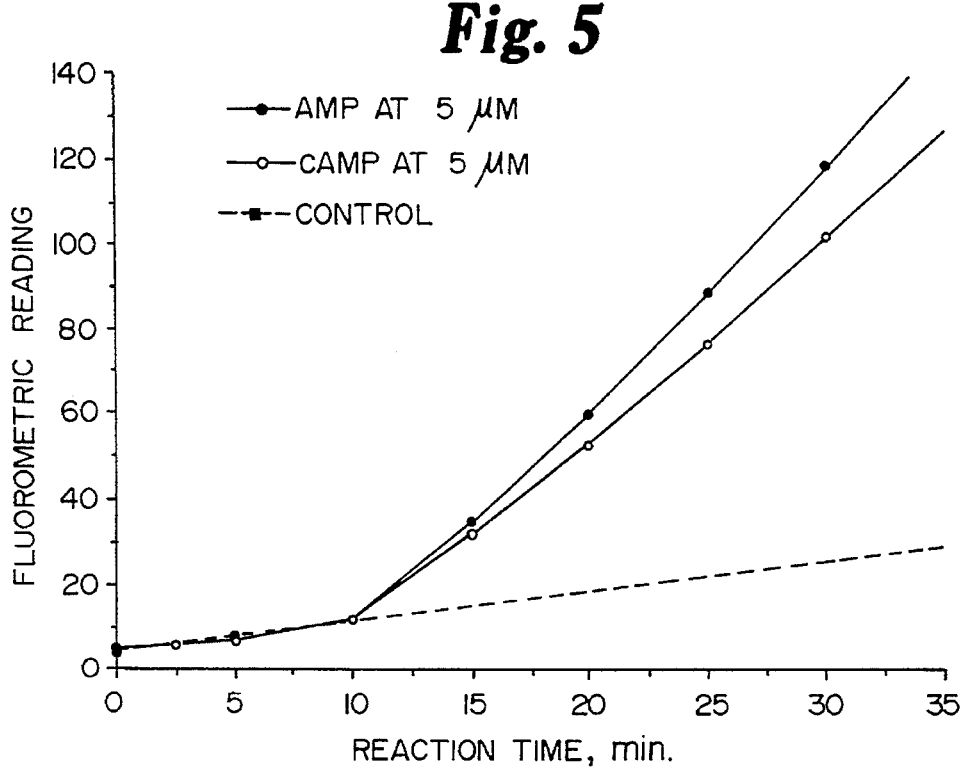
FIG. 5 is a graphical depiction of the time course of NADPH fluorescence produced by stimulation of glycogen phosphorylase a by AMP (o), cAMP (●) and control buffer (■).

As shown in FIG. 5, without AMP or cAMP, the basal reaction in control buffer remained low. The present fluorometric assay for AC activity relies on the principle that stimulation of glycogen phosphorylase a by AMP results in a concentration-dependent increase in phosphorylase a activity by reducing the $K_m$ for both glycogen and phosphate. As can be seen from the data presented in FIG. 5, the activation of glycogen phosphorylase a by cAMP is essentially identical to that caused by AMP.

EXAMPLE 6

Removal of AMP by the Cleaning Reactions.

Figure 6:
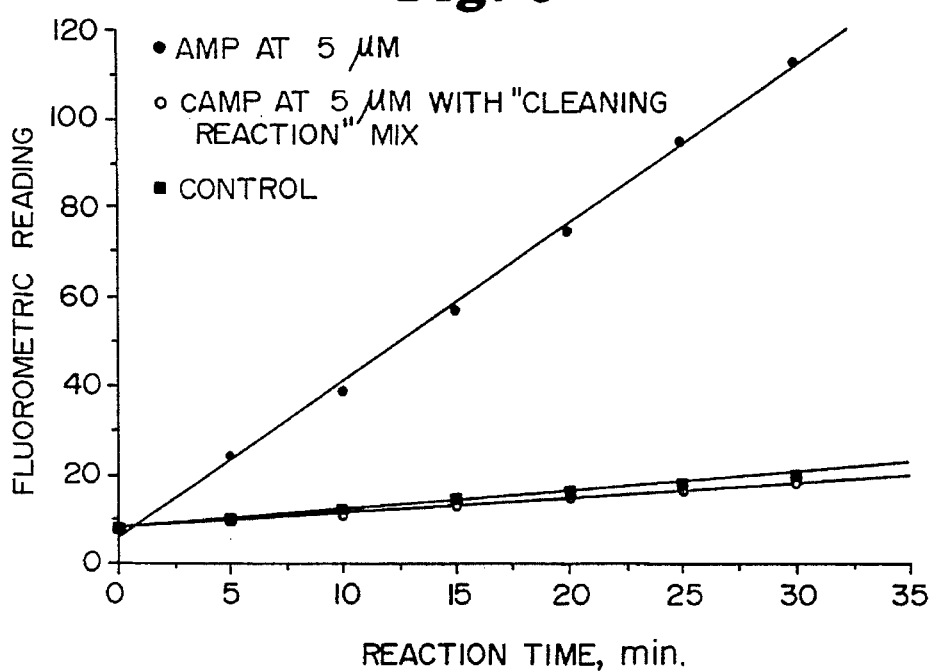
FIG. 6 is a graphical depiction of the time course of NADPH fluorescence produced by stimulation of glycogen phosphorylase a by AMP (●), AMP with prior pre-treatment with "cleaning reaction" mixture (o), and control buffer (■).

The effectiveness of the enzymatic "cleaning reactions" shown in Table 1 is demonstrated by the kinetic data shown in FIG. 6. AMP was incubated for 60 min at 37° C. with 50 μl of either buffer (100 mM Tris-HCl, pH 8.0) or a cleaning reaction mixture containing 100 mM Tris-HCl, pH 8.0; 5 mM $MgCl_2$. 2 mM $CaCl_2$, 0.02 units/ml apyrase; 0.025 units/ml 5'-nucleotidase and 0.1 mg/ml adenosine deaminase. After heating at 90° C. for 5 min, 950 μl of the glycogen→NADPH "cAMP mixture" of Example 2 was added, and the reaction allowed to proceed at 25° C.

The data on FIG. 6 demonstrate that when AMP is added to this reaction system without the cleaning step, glycogen phosphorylase a activity is markedly stimulated. However, when AMP is added in the presence of the cleaning reaction mixture, glycogen phosphorylase a activity remains similar to the control buffer values, due to the degradation of the AMP.

EXAMPLE 7

Fluorometric cAMP Measurement in Tissue

The following example illustrates the methodology employed to measure endogenous cAMP fluorometrically in tissue without agonist stimulation of cAMP synthesis.

Frozen heart tissue (0–1000 mg) was homogenized in ten volumes of 2°–4° C. 0.1M NaOH and 2.0 μl portions of the homogenate distributed into five reaction tubes. To each tube was added 4, 8 and 16 pmoles cAMP, as an internal control. To create the standard curve for cAMP, 0, 4, 8 and 16 pmoles of cAMP were added to five tubes each containing 2.0 μl 0.1M NaOH.

Into these tubes was introduced 25 μl of the cleaning reaction mixture shown on Table 4.

TABLE 4

| Cleaning Reaction Mixture | | |
|---|---|---|
| Compound | Concentration | Use (3.0 ml) |
| Tris-HCl pH 8 | 50 mM | 150 μl |
| $MgCl_2$ | 5 mM | 75 μl |
| $CaCl_2$ | 2 mM | 30 μl |
| 5'-Nucleotidase | .025 μl/ml | 30 μl |
| Apyrase | .02 μl/ml | 30 μl |
| Adenosine Deaminase | .1 mg/ml | 30 μl |
| $H_2O$ | — | 2.70 ml |

All tubes were incubated for 30 min at 37° C., and then heated at 95° C. for 15 minutes. Then, 200 μl of the cAMP reaction mixture shown on Table 5 was added to each tube.

TABLE 5

| cAMP Reaction Mixture | | |
|---|---|---|
| Compound | Concentration | Use (25.0 ml) |
| Imidazole pH 6.9 | 50 mM | 1.25 ml |
| $MgCl_2$ | 0.50 mM | 63 μl |
| EDTA | 1 mM | 250 μl |
| BSA | 0.004% | 25 μl |
| $K_2HPO_4$ | 1.5 mM | 38 μl |
| Glycogen | 0.25 mM | 438 μl |
| G-1,6-P | 2 μM | 50 μl |

TABLE 5-continued

| cAMP Reaction Mixture | | |
|---|---|---|
| Compound | Concentration | Use (25.0 ml) |
| NADP+ | 0.15 mM | 38 µl |
| DTT | 0.5 mM | 125 µl |
| Phosphodiesterase | 13.5 µg/ml | 33.8 µl |
| G-6-P-Dehydrogenase | 2.5 µg/ml | 11.3 µl |
| Phosphoglucomutase | 4.5 µg/ml | 11.3 µl |
| Glycogen Phosphorylase a | 2.2 µg/ml | 8.0 µl |
| H$_2$O | | 22.7 ml |

Figure 7:
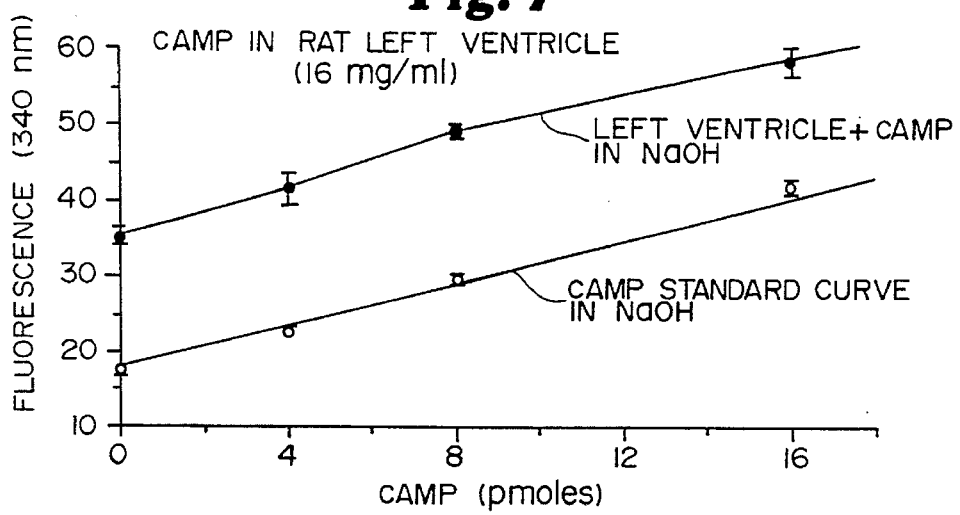
FIG. 7 is a graphical depiction of the fluorescence measured for left ventricle tissue samples plus added cAMP in NaOH (●) and of the fluorescence measured for standard cAMP samples in NaOH (o), in accord with the present method.

The tubes were incubated for 90 minutes at 31° C., 800 µl of AMP$_2$ buffer (50 mM, pH 9.9) was added, and the fluorescence measured at 340 nm. The data was plotted to yield the graph of FIG. 7, which yielded a plot (●) for the internal controls that was consistently elevated above the cAMP standard plot. From this plot, it could be determined that this tissue sample contained 12 pmol of cAMP.

EXAMPLE 8

Micro, cAMP-Measurement in Tissue

This example illustrates an adaption of the present assay so that cAMP can be measured in the range of 0–1000 fmol. The Cleaning Reaction Mixture employs glucose oxidase and alpha-amylase to remove endogenous glycogen. The assay also comprises amplifying the NADPH formed by the reactions shown on Table 1, hereinabove, using a cycling system utilizing glucose-6-P dehydrogenase and glutamate dehydrogenase, as generally disclosed by O. Lowry et al., in *Flexible System of Enziymatic Analysis*, Academic Press, New York (1972) at pages 130–135.

Frozen rat heart tissue is sectioned (20 µ thick) in a cryostat and freeze-dried at −40° C. Pieces of tissue from four different regions of the heart (six pieces/region), (2–4 µg each) are cut and placed in Teflon® block wells. To each piece, 0.2 µl of 20 mM aqueous NaOH is added. To generate standard curves, cAMP samples in the appropriate range (0, 40, 80, 160 and 320 and 0, 125, 250, and 1000 fmol/0.2 µl) are prepared in 20 mM NaOH and pipetted into eight other wells. All of the wells are then covered with a mixture of 40% n-hexadecane and 60% light mineral oil to prevent evaporation. The wells are heated to 80° C. for 20 minutes and then cooled to 25° C. Cleaning reaction mixture (Table 6) (0.4 µl) is added to each well and the reaction allowed to proceed for 30 min. at 37° C., then stopped by heating at 80° C. for 30 minutes.

TABLE 6

| Cleaning Reaction Mixture | | |
|---|---|---|
| Compound | Concentration | Use |
| Tris HCl pH 8.0 | 75 mM | 30 µl |
| MgCl$_2$ | 5 mM | 10 µl |
| CaCl$_2$ | 2 mM | 4 µl |
| 5'-Nucleotidase | 5 u/ml | 8 µl |
| Apyrase | 2 u/ml | 8 µl |
| Adenosine Deaminase | 4 u/ml | 8 µl |
| Glucose-oxidase | 50 u/ml | 4 µl |
| α-Amylase | 63 u/ml | 10 µl |
| H$_2$O | | 338 µl |

To all wells, 0.6 µl of cAMP reaction mixture (Table 7) is added and the wells incubated for 2 hours at 31° C.

TABLE 7

| cAMP Reaction Mixture | | |
|---|---|---|
| Compound | Concentration | Use |
| Imidazole pH6.9 | 75 mM | 375 µl |
| MgCl$_2$ | 0.5 mM | 12.5 µl |
| EGTA | 2 mM | 100 µl |
| Glycogen | 0.2 mM | 14.7 µl |
| BSA | 0.01% | 12.5 µl |
| DTT | 0.5 mM | 25 µl |
| G-1,6-P | 2 µM | 10 µl |
| NADP+ | 0.3 mM | 15 µl |
| P$_i$ | 0.2 mM | 10 µl |
| H$_2$O | | 4.41 ml |
| Phosphodiesterase | 300 µg/ml | 12 µl |
| Glucose-6-P$_i$-Dehydrogenase | 25 µg/ml | 2 µl |
| Phosphogluco-Mutase | 50 µg/ml | 2 µl |
| Glycogen Phosphorylase a | 2 µg/ml | 8 µl |

At the completion of the incubation, one µl of 0.45N NaOH is added to each well and the wells are again heated for 30 minutes at 80° C.

One µl reaction mixture from each well is transferred into 10×75 mm fluorometric tubes. The internal cycling reaction standards (0, 1, 2 and 4) pmoles NADP+, are prepared in duplicate, as shown in Table 8, and assayed in separate tubes concurrently as a control.

TABLE 8

| Cycling Reaction Standards | | |
|---|---|---|
| | NADP+(0.5 µM) | |
| Tube | Vol. | Concentration |
| 1–2 | 0 µl | 0 pmoles |
| 3–4 | 2 µl | 1 pmoles |
| 5–6 | 4 µl | 2 pmoles |
| 7–8 | 8 µl | 4 pmoles |

Fifty µl of the cycling reaction mixture (Table 9) are added to each robe, and the tubes are incubated at 37° C. for 60 min.

TABLE 9

| Cycling Reaction Mixture (5 ml) | | |
|---|---|---|
| Compound | Working | Use |
| Tris-Acetate pH 8.0 | 0.1 M | 500 µl |
| Ammonium acetate | 10 mM | 50 µl |
| α-Ketoglutarate | 10 mM | 500 µl |
| BSA | 0.04% | 50 µl |
| G-6-P | 10 mM | 500 µl |
| ADP | 1 mM | 50 µl |
| Glutamate-Dehydrogenase | 30 µg/ml | 15 µl |
| Glucose-6-P$_i$-Dehydrogenase | 5 mg/ml | 5 µl |
| H$_2$O | | 3.35 ml |

The rack containing the robes is placed in a 95° C. water bath for 5 minutes. Indicator reaction standards, 0–4 nmoles 6-PG, are prepared in duplicate, as shown on Table 10, and are assayed in separate tubes concurrently as a control.

TABLE 10

| Indicator Reaction Standards (6-P-G, 0.5 mM) | | |
|---|---|---|
| Tube | Vol. | Concentration |
| 1–2 | 0 µl | 0 nmoles |
| 3–4 | 2 µl | 1 nmoles |
| 5–6 | 4 µl | 2 nmoles |
| 7–8 | 8 µl | 4 nmoles |

Each tubes then receives 900 µl of indicator reaction mixture (Table 11 and are allowed to incubate for 30 min at 25° C. The fluorescence is then measured at 340 nm.

TABLE 11

| Indicator Reaction Mixture (100 ml) | | |
|---|---|---|
| Compound | Concentration | Use |
| Tris-HCl pH 8.0 | 50 mM | 5 ml |
| EDTA | 0.1 mM | 50 µl |
| Ammonium acetate | 30 mM | 3 ml |
| $MgCl_2$ | 5 mM | 2.5 ml |
| $NADP^+$ | 0.2 mM | 200 µl |
| 6-$P_i$-Gluconate-Dehydrogenase | 2.5 µg/ml | 25 µl |
| $H_2O$ | | 91.925 ml |

Figure 8:
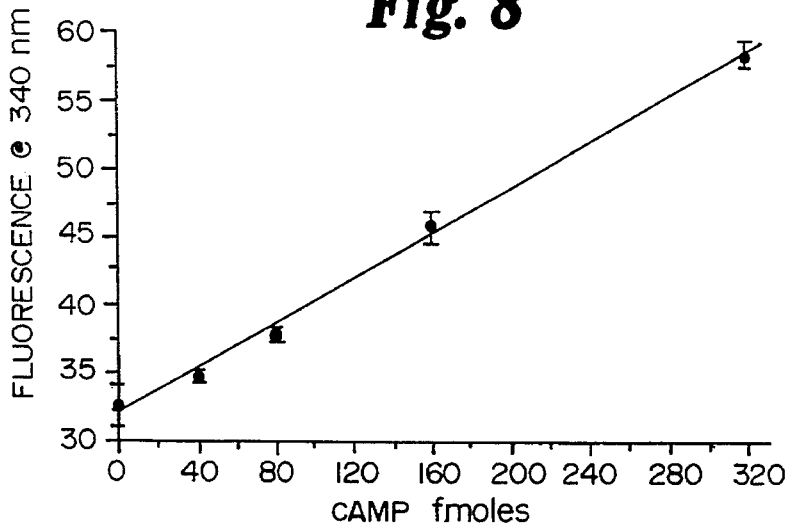
FIG. 8 is a graphical plot of fluorescence against concentration of standard samples of cAMP as determined by an embodiment of the invention.
Figure 9:
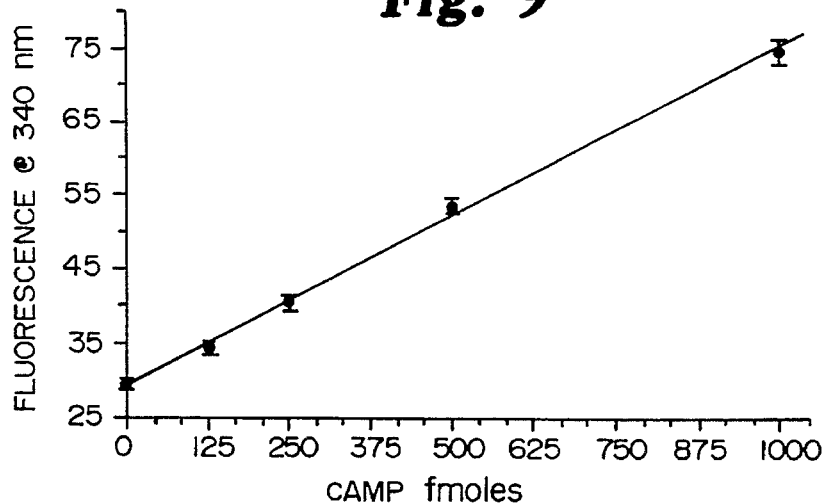
FIG. 9 is a graphical plot of fluorescence against concentration of standard samples of cAMP as determined by an embodiment of the invention.
Figure 10:
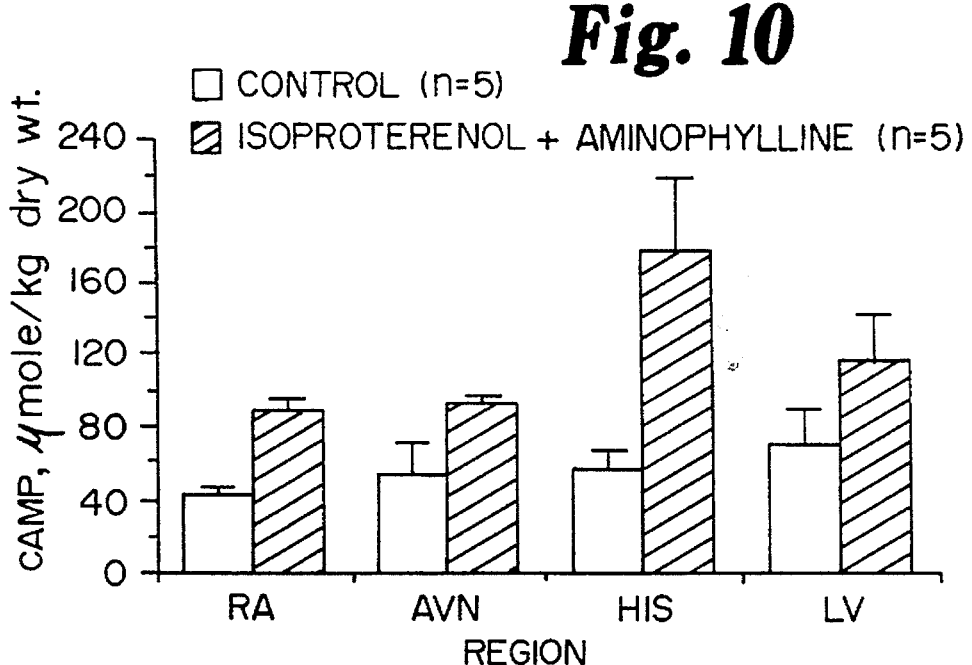
FIG. 10 is a graphical plot of the amount of cAMP in four regions of the rate heart (untreated=clear; drug-treated= shaded) as determined by the present method.

As depicted in FIGS. 8 and 9, the fluorescence measured for the control cAMP samples yielded linear plots over 40–1000 fmoles of cAMP. As shown in FIG. 10, when performed on tissue from five rats (control) or five rats pretreated 15 min before sacrifice with 0.33 µg/kg isoproterenol plus 20 µg/kg aminophylline, this assay is effective to measure the cAMP concentration in four regions of the heart (right atrium—RA; atfioventricular node—AVN; his bundle—HS; and the left ventricule—LV).

EXAMPLE 9

Micro cAMP Measurement in Tissue with ATP-ADP Double Cycling.

Frozen tissue is sectioned (20 microns thick) in a cryostat and freeze-dried at –40° C. Six pieces, weighing 2–4 g, for each tissue type are cut and placed into Teflon block wells, and aqueous of 20 mM NaOH (0.2 µl) is added to each well. cAMP standards (0, 125, 250 and 507 fmoles/0.2 µl) are prepared in 20 mM NaOH and pipetted into three wells (one well contains only 0.2 µl NaOH). All of the Teflon wells are then covered with oil (40% n-Hexadecane and 60% light mineral oil). The aqueous mixtures are heated at 80° C. for 30 minutes and then allowed to cool to 25° C. To all wells, 0.4 µl of cleaning reaction mixture of Table 12 is added and the reaction allowed to proceed for 60 minutes at 37° C., then heated at 80° C. for 30 minutes.

TABLE 12

| Cleaning Reaction Mixture | | |
|---|---|---|
| Compound | Final Reaction Concentrations | Use |
| Tris HCl pH 8.0 | 75 mM | 30 µl |
| $MgCl_2$ | 5 mM | 10 µl |
| $CaCl_2$ | 2 mM | 4 µl |
| 5'-Nucleotidase | 5 µ/ml | 8 µl |
| Apyrase | 2 µ/ml | 8 µl |
| Adenosine Deaminase | 4 µ/ml | 8 µl |
| $H_2O$ | | 332 µl |
| | | 400 µl |

To all wells, 0.6 µl of the pyruvate kinase reaction mixture of Table 13 is added and the Teflon block is incubated for 120 minutes at room temperature.

TABLE 13

| PK Reaction Mixture | | |
|---|---|---|
| Compound | Final Reaction Concentrations | Use |
| Imidazole pH 6.9 | 100 mM | 500 µl |
| $MgCl_2$ | 2 mM | 50 µl |
| KCl | 50 mM | 250 µl |
| Phospho(Enol)Pyruvate | 5 mM | 50 µl |
| Bovine Serum Albumin | 0.01% | 12.5 µl |
| Dithiothreitol | 0.5 mM | 25 µl |
| ATP | 150 nM | 75 µl |
| $H_2O$ | | 4.0 ml |
| Pyruvate Kinase | 20 µg/ml | 2 µl |
| Myokinase | 4 µg/ml | 2 µl |
| Phosphodiesterase | 20 µg/ml | 2 µl |

At the completion of this incubation, 1 µl of First Cycling Mix of Table 14 is added to each well and the reaction mixtures incubated for 60 minutes at 25° C.

TABLE 14

| First Cycling Mixture | | |
|---|---|---|
| Compound | Final Reaction Concentrations | Use |
| Tris-HCl pH 8 | 50 mM | 50 µl |
| KCl | 50 mM | 50 µl |
| $MgCl_2$ | 2 mM | 100 µl |
| Fructose | 5 mM | 50 µl |
| Bovine Serum Albumin | .01% | 2.5 µl |
| $NADP^+$ | 0.2 mM | 2 µl |
| Hexokinase | 47 µg/ml | 4.7 µl |
| Phosphoglucose Isomerase | 40 µg/ml | 4 µl |
| Glucose-6-Phosphate dehydrogenase | 10 µg/ml | 2 µl |
| $H_2O$ | | 734.8 µl |
| | | 1.0 ml |

To all wells, 1 µl of 0.45N NaOH is added and the Teflon block is heated at 80° C. for 30 minutes. Two µl from each well in transferred into fluorometric tubes. Cycling reaction standards, 0–4 pmoles $NADP^+$, were prepared in duplicate, as shown in Table 14, to serve as a control.

TABLE 15

| Cycling Reaction Standards ($NADP^+$ 0.5 mM) | | |
|---|---|---|
| Tube No. | Volume | Concentration |
| 1–2 | 0 µl | 0 pmoles |
| 3–4 | 2 µl | 1 pmoles |
| 5–6 | 4 µl | 2 pmoles |
| 7–8 | 8 µl | 4 pmoles |

To all tubes, 50 µl of the Second Cycling Reaction Mix of Table 16 is added, and the tubes incubated at 37° C. for 60 minutes, then the rack containing the tubes is placed in a 95° C. water bath for 5 min.

TABLE 16

Second Cycling Mix

| Compound | Final Reaction Concentrations | Use |
| --- | --- | --- |
| Tris-Acetate pH 8.0 | 0.1 M | 500 μl |
| Ammonium acetate | 10 mM | 50 μl |
| α-Ketoglutarate | 10 mM | 500 μl |
| Bovine Serum Albumin | 0.04% | 50 μl |
| Glucose-6-Phosphate | 10 mM | 500 μl |
| ADP | 1 mM | 50 μl |
| Glutamate dehydrogenase | 30 μg/ml | 15 μl |
| Glucose-6-Phosphate dehydrogenase | 5 μg/ml | 5 μl |
| H$_2$O | | 3.35 ml |
| | | 5.0 ml |

Indicator reaction standards, 0–4 nmoles 6-phosphogluconolactone (6-PG), are prepared in duplicate, as shown on Table 17, as a control.

TABLE 17

Indicator Reaction Standards (6-P-G 0.5 mM)

| Tube | Vol. | Conc. |
| --- | --- | --- |
| 1–2 | 0 μl | 0 nmoles |
| 3–4 | 2 μl | 1 nmoles |
| 5–6 | 4 μl | 2 nmoles |
| 7–8 | 8 μl | 4 nmoles |

All tubes receive 900 μl of indicator mix of Table 18, and are allowed to incubate for 30 minutes at 25° C.

TABLE 18

Indicator Reaction Mix

| Compound | Final Reaction Concentrations | Use |
| --- | --- | --- |
| Tris-HCl pH 8.0 | 50 mM | 5 ml |
| EDTA | 0.1 mM | 50 μl |
| Ammonium acetate | 30 mM | 3 ml |
| MgCl$_2$ | 5 mM | 2.5 ml |
| NADP$^+$ | 0.2 mM | 200 μl |
| 6-Phospho Gluconate dehydrogenase | 2.5 μg/ml | 25 μl |
| H$_2$O | | 91.925 ml |
| | | 100.0 ml |

Figure 11:
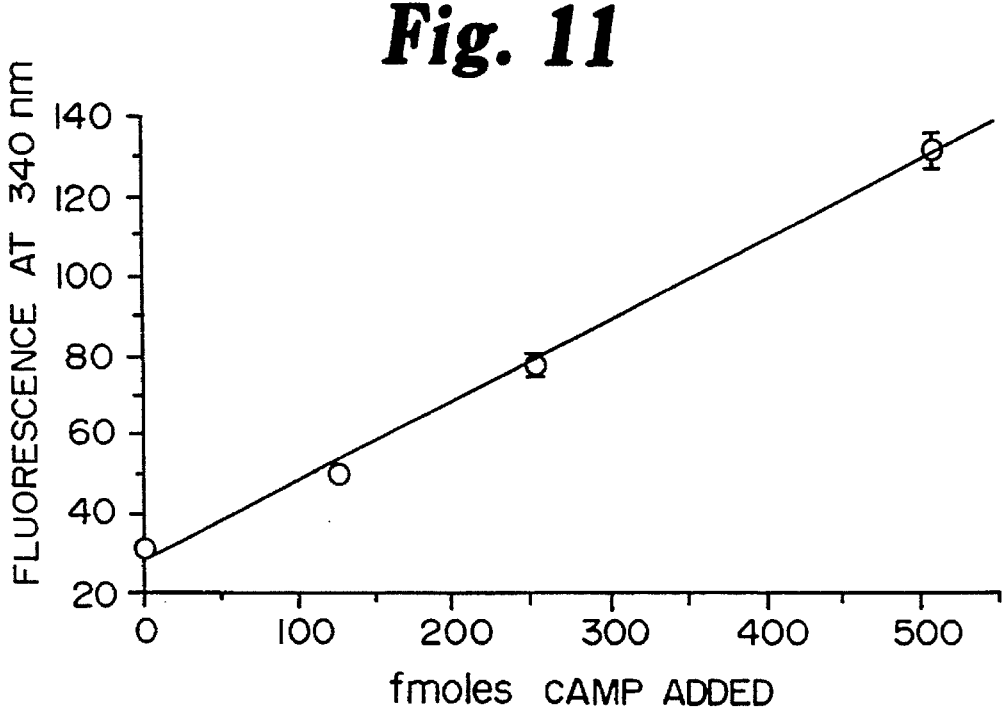
FIG. 11 is a graphical plot of fluorescence against concentration of standard samples of cAMP as determined by an embodiment of the invention.

The fluorescence is measured at 340 nm, to afford the standard curve shown on FIG. 11, demonstrating the ability of the present assay to quantify cAMP in the fmol range.

EXAMPLE 10

Micro cAMP Measurement in Tissue Cultures with Alternative Cleaning Reactions and ATP and ADP Double Cycling reactions This example illustrates an adaption of the present assay so that cAMP can be measured in the range of less than 20 fmol. The assay comprises the additional step of removal of all endogenous glucose-6-phosphate using a cleaning reaction mixture which contains alkaline phosphatase.

Part A. Ventricular myocyte preparation

Isolated ventricular myocytes were obtained from hearts of 1-day-old rats, grown in primary cultures, and harvested by brief alternating cycles of room temperature trypsinization and mechanical dissociation. There were approximately 5 million viable myocardial cells per heart. After plating at a density of approximately 1 million cells per 100 mm, dish cells were grown in minimum essential medium with Hanks balanced salt solution containing 5% bovine calf serum cells. Simpson et at., *Circ. Res.*, 51, 787–801 (1982). On day 4, the medium was changed. The cultures contained >90% myocardial cells and cell numbers were constant over time. Simpson et at., cited supra.; Rocha-Singh et at., *J. Clin. Invest.*, 88, 204–213 (1991); and Rocha-Singh et at., *J. Clin. Invest.*, 88, 706–766 (1991).

In these studies, six plates of myocytes were randomized into two groups (n=3 plates/group). The phosphodiesterase inhibitor 3-isobutyl-1-methylxanthine (IBMX) was added to the medium of each group to achieve a 2 μM final concentration. After 5 minutes, isoproterenol was added to the stimulated group to achieve a final 1 μM concentration, while the control group received no additional drug. After 5 minutes, cells from all six plates and plates of culture medium without cells were eluted with a total of 5 ml of 100% ethanol. One-tenth of the eluent (0.5 ml) from each dish was removed and air dried in a 12×75 mm borosilicate glass tube and stored at −80° C. The other 4.5 ml were similarly air dried and stored. At the time of assay, the pellet was thawed and resuspended in 100 μl of 0.5N perchlode acid. The extracts were vortexed at 4° C. for 2 minutes and sonicated for 1 minute using a sonicator (Branson Cleaning Equipment Co. A Smith-Kline Co., USA). The extract was neutralized with 25 μl of 2N KOH, centrifuged at 2000 g for 30 minutes and 80 μl of supernatant was removed for assay.

Part B. Enzymatic fluorometric assay

This 5-step assay utilizes the following series of reactions:

Step 1: Cleaning Reactions

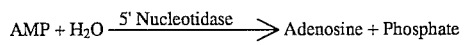

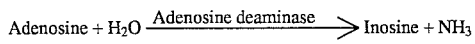

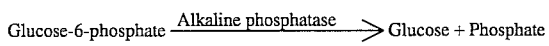

A volume of 3 μl of neutralized myocyte extract (either 2.4% or 0.24% of total eluent from a 100 mm plate) or 3 μl of a known amount of cAMP standard was added into a 10×57 Pyrex® assay tube. While at room temperature, 25 μl of "cleaning" reaction mix (100 mM Tris-HCl, pH 8.0; 2 mM MgCl$_2$; 2 units/ml apyrase; 2.5 units/ml 5′ nucleotidase; 0.1 mg/ml adenosine deaminase; 20 units/ml alkaline phosphatase) were added to each assay tube. The mixture was incubated at 37° C. for 1 hour. Enzymes were then deactivated by heating for 30 minutes at 90° C. A set of duplicate samples was similarly assayed and used for an internal tissue blank control.

Step 2. Conversion of cAMP

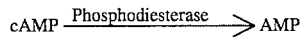

A volume of 25 μl of a phosphodiestemse-containing reaction mix (25 mM Tris-HCl, pH 8.0; 2 mM MgCl$_2$; 0.02% bovine serum albumin; 40 μg/ml phosphodiesterase)

was added to each assay tube from Step 1. A tissue blank was generated by adding buffer (25 mM Tris-HCl, pH 8.0; 2 mM MgCl$_2$; 0.02% bovine serum albumin) without phosphodiesterase to parallel the set of samples from Step 1. After 30 minutes at 37° C., the reactions were terminated by heating the assay tubes at 90° C. for 5 minutes.

Step 3. Conversion of AMP to ATP

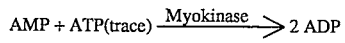

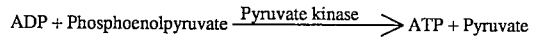

A volume of 25 µl of myokinase reaction mix (25 mM Tris-HCl, pH 8.0; 2 mM MgCl$_2$; 225 mM KCl; 20 nM ATP; 8 mM phosphoenolpyruvate; 2 mM dithiothreitol; 0.01% bovine serum albumin; 24 µg/ml myokinase; 50 µg/ml pyruvate kinase) was added to each assay tube from Step 2. The reactions were incubated for 5 hours at room temperature.

Step 4: Enzymatic Cycling

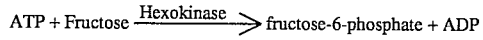

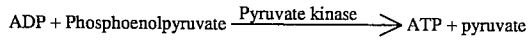

A volume of 25 µl of hexokinase reaction mix (50 mM Tris-HCl, pH 8.0; 2 mM MgCl$_2$; 8 mM fructose; 0.01% bovine serum albumin; 350 µg/ml pyruvate kinase; 400 µg/ml hexokinase) was added to each assay tube from Step 3. In view of the high concentrations of enzymes per reaction, it was important to set up these reactions at 0° C. to insure the same starting time for all assay tubes. After a 3-hour incubation at 37° C., the reactions were terminated by heating at 90° C. for 5 minutes.

Step 5. Generation of NADPH

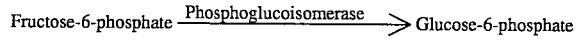

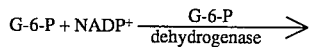

6-phosphogluconolactone + NADPH + H$^+$

A volume of 800 µl of indicator reaction mix (50 mM Tris-HCl, pH 8.0; 100 µM NADP+; 2 µg/ml phosphoglucoisomerase; 1 µg/ml glucose-6-phosphate dehydrogenase) was added to the assay tubes from Step 4. After 15 minutes at room temperature, the final concentration of NADPH was measured using a fluorometer (Optical Technology Devises, Inc., New York). The fluorometer was set such that a reading of 10 fluorometric units was equivalent to 1 nmol of NADPH in 900 µl of buffer (50 mM Tris-HCl, pH 8.0). Individual assay steps were verified by concurrently assaying internal controls using known concentrations of the appropriate substrate (for example, additional ATP was used to check the "cleaning" reactions, an AMP standard curve was used to assess Step 3, and an ATP standard curve was used to assess Step 4).

Part C

Figure 12:
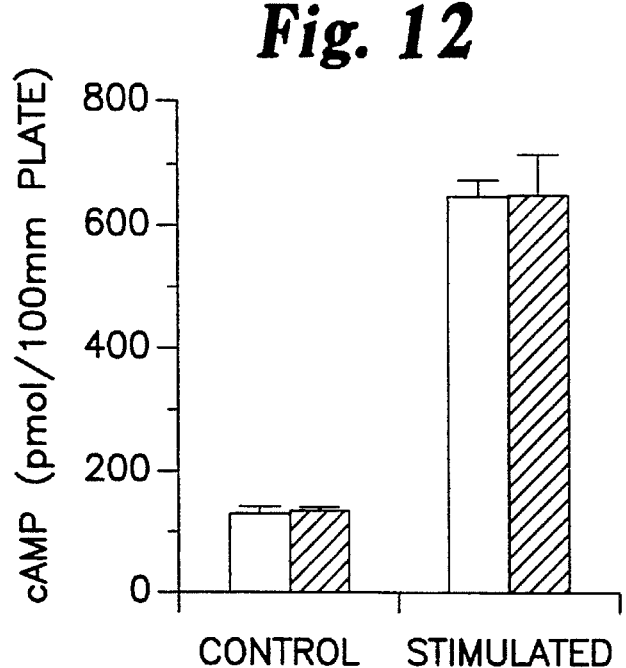
FIG. 12 is a graphical depiction of the amount of cAMP detected in untreated and stimulated cells as determined by the present fluorometric method (clear) and a commercially available immunocolorimetric assay (shaded).

Results Measurement of the fluorescence at 340 nm afforded the standard cAMP curve shown in FIG. 12. When assaying cAMP in the 4–40 pmol range, assay sensitivity can be decreased by using a 1 hour cycling time and a 10-fold lower concentration of hexokinase and pyruvate kinase in reaction Step 4. In this specific concentration range, a higher concentration of ATP (a final concentration of 4 pmol) can be used in Step 3 and the time needed to complete Step 3 can be reduced to 2 hours. Thus, the less sensitive form of this assay (>4 pmoles cAMP/sample) can be conveniently performed in 6 hours. A 3-hour cycling time was used in Step 4 to increase assay sensitivity, which allowed differences as small as 20 fmol to be detected between different samples.

The measurement of cAMP in control and isoproterenol-stimulated cells using both this new fluorometric assay and a commercially available radioimmunoassay and immuno-colorimetric assays are shown in FIG. 12. The measured values are similar with both techniques. The data shown in FIG. 12 were generated from measurements of 1/10 of the eluent from each plate of cells. For both methods of cAMP measurement, results of multiple analyses of a single sample did not differ by more than 10% with variability usually less than 5%. Finally, further assay sensitivity can be obtained by utilizing adenylate kinase (equivalent in catalytic activity to muscle derived myokinase) purified from liver. Hamada et al., *Biol. Chem.*, 260, 11595 (1985). Instead of using trace amounts of ATP to initiate the conversion of AMP to ADP in Step 3 (p 37, line 9), this reaction, when using purified liver myokinase (also termed adenylate kinase) can be initiated using picomole amounts of UTP. This will both increase assay sensitivity and decrease the time needed to complete this reaction, thereby decreasing overall assay time and increasing overall assay sensitivity, when needed.

EXAMPLE 11

Determination of Endogenous Phosphodiesterase

Tissue was dissolved in 0.1 µl of SET buffer. A volume of 0.2 µl of PDE mix (Tris-HCl 50 mM, pH 7.5, cAMP 50 µM) was added and incubated at 37° C. for 20 minutes. The oil rack was heated at 80° C. for 30 minutes. A volume of 0.4 µl of "cleaning" mix was added and incubated at 37° C. for 1 hour. The oil rack was heated at 80° C. for 30 minutes. A volume of 1 µl of cAMP reaction mix was added and incubated for 1 hour at room temperature. The resultant NADPH was amplified by NADP+/NADPH cycling.

Figure 13:
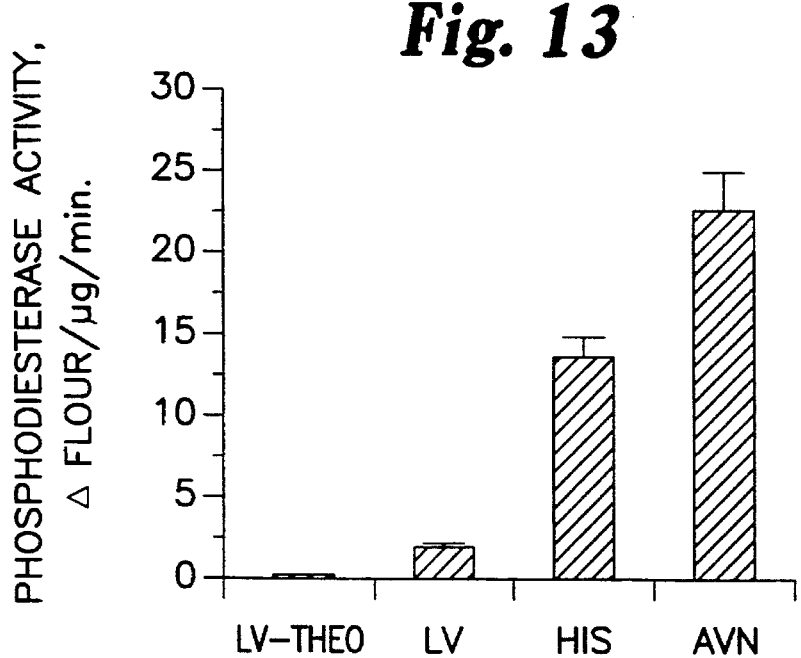
FIG. 13 is a graphical depiction of phosphodiesterase activity found in various physiological samples (LV-Theo= Left ventricle with theophylline; LV=Left Ventricle; His= His bundle; AV=AV node) as determined by the present method.

As shown in FIG. 13, when performed on tissue from rat hearts, this assay is effective to measure the phosphodiesterase concentration in three regions of the heart (LV—left ventricle; LV-Theo—Left ventricle treated with theophylline; HIS—His bundle; AVN—atrioventricular node).

EXAMPLE 12

Enzymatic Fluorometric Assay utlizing ATP-ADP Enzyme Cycling Reactions compared with Radioimmunoassay and Radioactive Adenylate Cydase Assay Adenylate cyclase activities of six different rabbit cardiac membranes under basal and drug treated conditions were assessed using the fluorometric method of the present invention, radioimmunoassay and original [alpha-$^{32}$P] ATP method developed by Salomon. The first part of the non-radioactive fluorescent technique for measuring adenylate cyclase activity is similar to the method described in Example 2 except that 3-isobutyl-1-methylxanthine (IBMX), rather than theophylline, was used to inhibit phosphodiesterase activity. Furthermore, a series of ATP-ADP enzyme-cycling reactions was used to amplify the cAMP signal, rather then the AMP stimulation of glycogen phosphorylase a utilized in previous examples. Use of the ATP- ADP enzymatic cycling amplification step can lengthen the assay duration, depending upon the desired assay sensitivity. However, ATP-ADP enzymatic cycling significantly increases assay sensitivity, enough to assess the inhibition of activity. Moreover, due to the potential variability from lot to lot of glycogen phosphorylase a, at least in the only presently commercially available form (Sigma Chemical Co.), the use of the ATP-ADP enzymatic cycling amplification step is more reliable when measuring less than 10 pmol of cAMP production/sample.

Enzymatic Fluorometric Assay

Part A

A volume of 1.0 µl of either $H_2O$, isoproterenol, NaF, guanylyl-5'-imidodiphosphate (GppNHp), carbachol, and adenosine was added to each of six reaction tubes on ice. Next, 25 µl of cyclase mix (100 mM Tris-acetate, pH 7.4; 4.2 mM KCl; 10 mM $MgCl_2$; 20 mM phosphoenolpyruvate; 2 mM ATP; 20 µM GTP; 2 mM dithiothreitol; 0.04% bovine serum albumin; 0.2 mM 3-isobutyl-1-methylxanthine (IBMX); 100 µg/ml pyruvate kinase) was added to each reaction tube. The stored membrane was diluted with SET buffer in a concentration of 1.5 mg of protein/ml. Finally, 25 µl of membrane suspension, which contained 37.5 µg of protein, was added to each tube, and the reaction was initiated by placing the tubes in a water bath maintained at 37° C. After 30 minutes, the reaction was terminated by heating at 90° C. for 5 minutes. Denatured protein was removed by centrifugation at 2000 g for 5 minutes and the supernatant was stored at −80° C. until the cAMP was measured. For internal cAMP standard, a volume of 1.0 µl of known amount of cAMP was added to each reaction tube. Then, 25 µl of cyclase mix and 25 µl of boiled membrane preparation were added to each tube. After 30 minutes, the reaction was terminated by heating at 90° C. for 5 minutes.

Part B

A volume of 5 µl of reaction of product from Part A was transferred to Pyrex® tubes. For external cAMP standard, a same volume of known amount of cAMP was also added to assay tubes. Newly synthesized cAMP was measured using the following enzymatic fluorometric assay.

1. A volume of 25 µl of "cleaning" reaction mix (100 mM Tris HCl, pH 8.0; 2 mM $MgCl_2$; 2 units/ml apyrase; 2.5 units/ml 5'-nucleotidase; 50 µg/ml adenosine deaminase; 20 units/ml alkaline phosphatase) was added to each assay tube. The mixture was incubated at 37° C. for 30 minutes. Enzymes were then destroyed by heating for 10 minutes at 90° C.

2. A volume of 25 µl of a phosphodiesterase-containing reaction mix (100 mM Tris-HCl pH 8.0; 2 mM $MgCl_2$; 0.01% bovine serum albumin; 60 µg/m; phosphodiesterase) was added to each assay tube from Step 1. After 60 minutes at 37° C., the assay tubes were heated at 90° C. for 5 minutes.

3. A volume of 25 µl of myokinase reaction mix (100 mM Tris-HCl, pH 8.0; 2 mM $MgCl_2$; 225 mM KCl; 200 nM ATP; 8 mM phosphoenolpyruvate; 2 mM dithiothreitol; 0.01% bovine serum albumin; 24 µg/ml myokinase; 50 µg/ml pyruvate kinase) was added to the assay tubes from Step 2. The reactions were incubated at 37° C. for 2 hours.

4. A volume of 25 µl of hexokinase reaction mix (100 mM Tris-HCl, pH 8.0; 2 mM $MgCl_2$; 8 mM fructose; 0.01% bovine serum albumin; 50 µg/m; hexokinase) was added to the assay tubes from Step 3 on ice. After a one hour incubation at 37° C., the reactions were terminated by heating at 90° C. for 5 minutes.

5. A volume of 800 µl of indicator reaction mix (50 mM Tris-HCl, pH 8.0; 200M $NADP^+$; 1 g/ml glucose-6-phosphate dehydrogenase) was added to the assay tubes from Step 4. After 15 minutes at room temperature, the final concentration of NADPH was measured using a fluorometer (Optical Technology Devices, Inc., New York). The fluorometer was set such that a reading of 1 fluorometric unit was equivalent to 100 pmol of NADPH in 900 µl of buffer (50 mM Tris-HCl, pH 8.0).

Radioimmunoassay

To confirm the accuracy and reliability of the enzymatic fluorometric assay, cAMP in the reaction product from the above experiment was also measured using commercially-available cAMP radioimmunoassay kits (Amersham). All samples were processed using nonacetylated methods.

Radioactive Adenylate Cyclase Assay using [alpha-$^{32}$P] ATP

Adenylate cyclase activity in the same membrane preparations was measured using the original radioactive adenylate cyclase assay developed by Salomon et al. Briefly, a volume of 10 µl of assay cocktail (40 mM Tris-Acetate, pH 7.5; 0.4 mM ATP; 15 mM $MgCl_2$; 2 mM cAMP; 8 mM theophylline; 130 µg/m; pyruvate kinase; 20 mM phosphoenolpyruvate; 5.5 mM KCl; 2–6×$10^8$ cpm/ml [alpha-$^{32}$P] ATP) was added to each reaction tube on ice. Next, 10 µl of 10 mM GTP was added. Then 10 µl of $H_2O$, isoproterenol, NaF, GppNHp, carbachol and adenosine were added. Finally, 20 µl of stored membrane suspension was added to each tube (final reaction volume is 50 µl). The reaction was initiated by placing the tubes in a water bath maintained at 37° C. After 30 minutes, the reaction was terminated by adding 100 µl of stopping solution (2% sodium lauryl sulfate, 45 mM ATP, 1.3 mM cAMP) and mixing. Test tubes were then heated in boiling water for 3 minutes. A volume of 50 µl of 8-$^3$H]cAMP solution was added to each test tube. The separation of the reaction product was achieved by sequential chromatography on Dowex 50 cation exchanger (Bio-Rad Laboratories, Calif., U.S.A.) and on neutral alumina (Bio-Rad Laboratories, Calif., U.S.A.) and the product was eluted into Ultima Gold™ scintillation fluid (Packard, Conn., U.S.A.). Recovery, as assessed by [8-$^3$H]cAMP, was 80–95%.

Carbachol, Adenosine, GppNHp, isoproterenol, NaF, phosphoenolpyruvate, IBMX, apyrase, 5'-nucleotidase, sucrose and fructose were obtained from Sigma Chemical Company. The [alpha-$^{32}$P]ATP and [8-$^3$H]cAMP were purchased from Amersham. Other enzymes and substrates were obtained from Boehringer-Mannheim Company.

Comparison of the Three Different Methods

Figure 14:
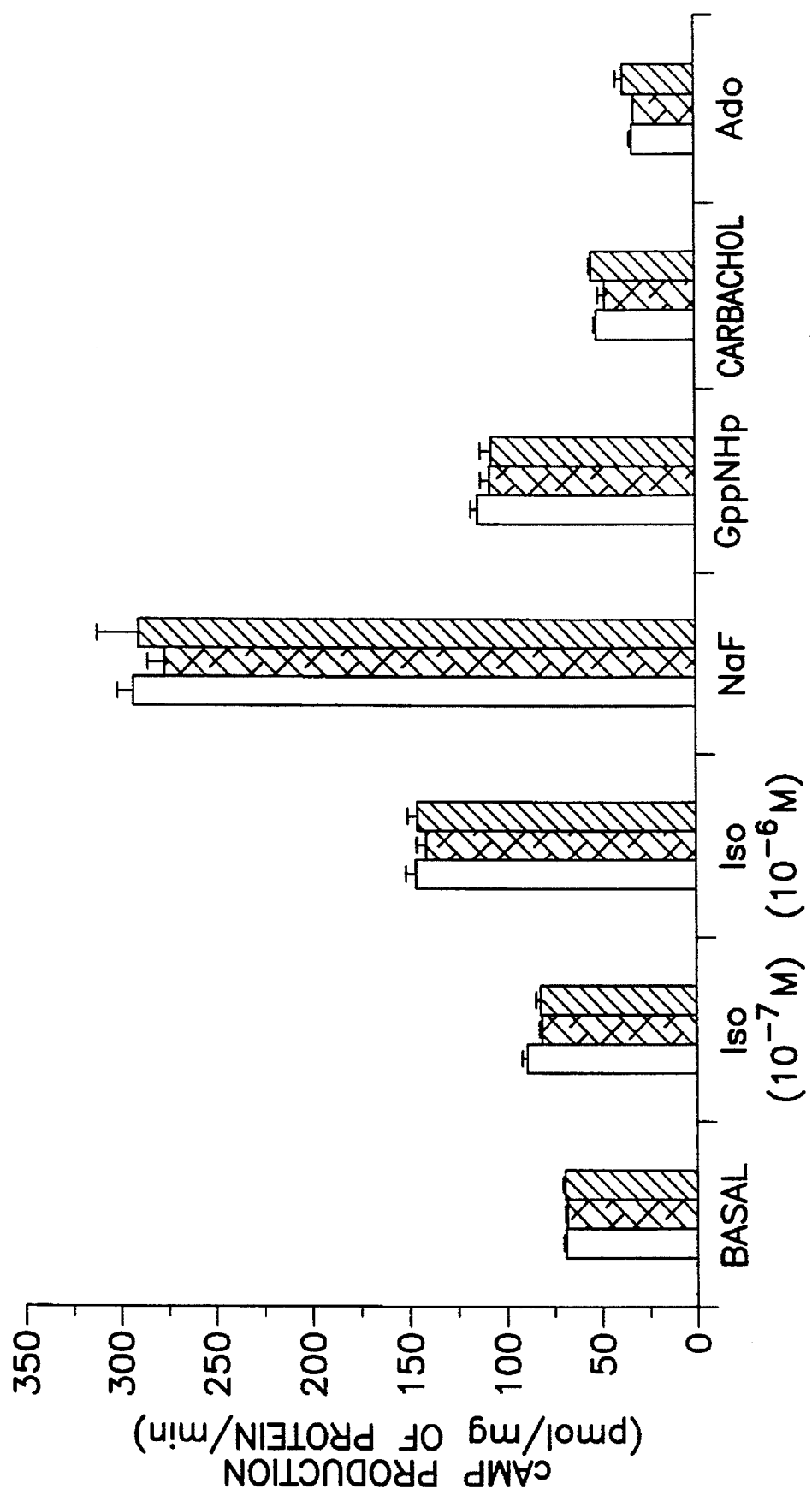
FIG. 14 is a graphical depiction of a comparison of basal, isoproterenol ($10^{-7}$M and $10^{-6}$M), NaF ($10^{-2}$M), GppNHp ($10^{-4}$M), carbachol ($10^{-6}$M) and adenosine ($10^{-3}$M) on adenylate cyclase activity using three different methods to measure the accumulation of cAMP (□=enzymatic fluorometric assay; ■=Salomon's method; ■=radioimmunoassay; Iso=isoproterenol; GppNHp=5'-guanylyl-imidodiphosphate; NaF=sodium fluoride; Ado=Adenosine).

Basal, isoproterenol ($10^{-7}$ and $10^{-6}$ M), NaF ($10^{-2}$ M), GppNHp ($10^{-4}$ M), carbachol ($10^{-6}$ M) and adenosine ($10^{-3}$ M) treated adenylate cyclase activities were assessed using enzymatic fluorometric assay, radioimmunoassay and original Salomon's method, as shown in FIG. 14. Isoproterenol increased cAMP production, in a concentration-dependent manner. NaF and GppNHp also increased production, while carbachol and adenosine inhibited it. The absolute values as well as the fold stimulation and/or inhibition were nearly identical among the three different methods.

Despite the similarity of results, the enzymatic fluorometric approach offers a number of potential advantages. The standard curve of fluorometric assay is linear and can be used over a broad concentration range. In contrast, the concentration range in which reliable measurements can be made with radioimmunoassay, is quite narrow and the standard curve is parabolic. The fluorometric assay is about 1/10 the expense on a cost/assay basis, compared with radioimmunoassay. The time required to perform the enzymatic fluorometric assay or the radioimmunoassay is similar, while Salomon's method requires a longer amount of time, often overnight, to complete the assay.

| TABLE OF ABBREVIATIONS | |
| --- | --- |
| Abbreviation | Chemical Name |
| ATP | adenosine 5'-triphosphate |
| ADP | adenosine 5'-diphosphate |
| AMP | adenosine 2'- and 3'-monophosphate |
| AC | adenylate cyclase |
| GTP | guanosine 5"-triphosphate |
| cAMP | adenosine 3',5'-cyclic monophosphate |
| Gpp(NH)p | guanylyl-5'-imidodiphosphate |
| EGTA | ethyleneglycol-bis-(β-aminoethyl ether)-N,N'-tetraacetic acid |
| $AMP_2$ | 2-amino-2-methylpropanol |
| BSA | bovine serum albumin |
| DTT | dithiothretol |
| ME | β-mercaptoethanol |
| Tris | tris(hydroxymethyl)aminoethane |
| NADP | β-nicotinamide adenine dinucleotide phosphate |
| NADPH | β-nicotamide adenine dinucleotide phosphate (reduced form) |
| PEP | phospho(enol)pyruvate |
| PK | phosphokinase |
| G-6-P | glucose-6-phosphate (glucose-6-P) |
| $P_i$ | inorganic phosphate |
| GGPDH | glucose 6-phosphate dehydrogenase |
| GDH | glutamic dehydrogenase |
| G-1,6-P | glucose-1,6-diphosphate |
| G-6-$P_i$-dehydrogenase | glucose-6-phosphate-dehydrogenase |
| AP | alkaline phosphatase |

What is claimed is:

1. A method of measuring an amount of adenylate cyclase (AC) in a sample of physiological material comprising:
   (a) combining a sample of physiological material comprising (i) cAMP produced by endogenous AC, (ii) other endogenous adenine nucleotides selected from the group consisting of ATP, AMP, ADP and mixtures thereof, and (iii) glucose-6-phosphate, with effective amounts of apyrase, 5'-nucleotidase and adenosine deaminase, to enzymatically eliminate said other endogenous adenine nucleotides in said sample and with an amount of alkaline phosphatase effective to enzymatically eliminate said glucose-6-phosphate in said sample;
   (b) enzymatically converting the cAMP to AMP; and
   (c) measuring the AMP without the use of radioactive reagents, said measurement indicating the amount of cAMP and AC in said sample.

2. The method of claim 1, further comprising in step (a), combining the sample with effective amounts of (i) glucose oxidase and alpha-amylase or (ii) glycogen phosphorylase a, to enzymatically eliminate endogenous glycogen from said sample.

3. The method of claim 1, wherein, in step (b), said AMP is employed to stimulate the enzymatic production of an amount of NADPH which is proportional to the amount of AMP present in the sample; and wherein in step (c) fluorometry, spectrofluorometry or spectrophotometry is employed to measure said amount of NADPH, to provide a measure of the adenylate cyclase and cAMP in said sample.

4. The method of claim 1 wherein the conversion of cAMP into AMP is carried out by combining the sample with an effective amount of phosphodiesterase.

5. The method of claim 1 wherein step (b) further comprises conversion of glycogen and inorganic phosphate added to the sample to glucose-1-phosphate by adding glycogen phosphorylase a.

6. The method of claim 5, wherein in step (b), the glucose-1-phosphate is converted into 6-phosphoglucono-lactone and NADPH by combining the sample with an amount of phosphoglucomutase effective to convert the glucose-1-phosphate to glucose-6-phosphate, and by combining the sample with an amount of glucose-6-phosphate dehydrogenase and $NADP^+$ effective to convert the glucose-6-phosphate to 6-phosphogluconolactone and NADPH.

7. The method of claim 6 further comprising, in step (c), heating the sample in the presence of water, so as to convert the 6-phosphogluconolactone into 6-phosphogluconate, and then adding an amount of $NADP^+$ to said sample which is effective to convert the 6-phosphogluconate into ribulose-5-phosphate and NADPH.

8. A fluorometric method to measure adenylate cyclase (AC) comprising:
   (a) combining a sample of a physiological material comprising (i) cAMP produced by endogenous AC, (ii) at least on other noncyclic adenine nucleotide; and (iii) glucose-6-phosphate; with a mixture of apyrase, 5'-nucleotidase, adenosine deaminase and alkaline phosphatase in aqueous buffer to from a reaction mixture so as to destroy at least on other adenine nucleotide and the glucose-6-phosphate, while retaining said cAMP in a resulting reaction mixture;
   (b) converting said cAMP to AMP by combining said reaction mixture with phosphodiesterase, glycogen, glycogen phosphorylase a, inorganic phosphate, phosphoglucomutase, glucose-6-phosphate dehydrogenase, glucose-1,6-diphosphate, $Mg^{2+}$ and $NADP^+$ so that said glycogen is converted into NADPH and 6-phosphogluconolactone; and
   (c) measuring the concentration of NADPH fluorometrically, said concentration of NADPH providing a measure of the concentration of cAMP and AC in said sample.

9. The method of claim 8 further comprising in step (a), combining the sample with effective amounts of (i) glucose oxidase and alpha-amylase or (ii) glycogen phosphorylase a, to enzymatically eliminate endogenous glycogen from said sample.

10. The method of claim 8 wherein steps (a) and (b) are combined.

11. The method of claims 8 or 9 further comprising, after step (b), converting said 6-phosphogluconolatone to ribulose-5-phosphate and NADPH by sequentially heating the reaction mixture and adding 6-phosphogluconate dehydrogenase and $NADP^+$ to the reaction mixture.

12. The method of claim 8 wherein said at least one other adenine nucleotide in step 1 comprises ATP, ADP, AMP, or a mixture of two or three thereof.

13. The method of claims or 8 or 9 wherein excess glucose-6-phosphate, excess alpha-ketoglutarate, glutamate dehydrogenase, and glucose-6-phosphate dehydrogenase are combined with the amount of NADPH prior to fluorometry so that the alpha-ketoglutarate is converted to glutamate and $NADP^+$, and the glucose-6-phosphate and the $NADP^+$ are converted to 6-phosphogluconolactone and NADPH.

14. The method of claim 13 wherein said 6-phosphogluconolactone is further hydrolyzed to 6-phosphogluconate and said 6-phosphogluconate is combined with $NADP^+$ in the presence of 6-phosphogluconate dehydrogenase to yield ribulose-5-phosphate and NADPH.

15. The method of claims 1 or 8 wherein the physiological material is mammalian tissue.

16. The method of claims 1 or 8 wherein the physiological material is a physiological fluid.

* * * * *

UNITED STATES PATENT AND TRADEMARK OFFICE
CERTIFICATE OF CORRECTION

PATENT NO. : 5,618,665
DATED : April 8, 1997
INVENTOR(S) : Keith G. Lurie et al.

It is certified that error appears in the above-identified patent and that said Letters Patent is hereby corrected as shown below:

On title Page, [63], please delete "Serial No. "7,847" and insert --007,847--

At Column 15, line 27, please center "EXAMPLE 5".

At Column 17, line 25, please delete "Micro cAMP-Measurement" and insert --micro-cAMP Measurement--.

At Column 28, line 17, please delete "on" and insert --one--.

At Column 28, line 20, please delete "from" and insert --form--.

Signed and Sealed this

Seventh Day of October, 1997

Attest:

BRUCE LEHMAN

Attesting Officer

Commissioner of Patents and Trademarks